US009428760B2

(12) United States Patent
Frohberg et al.

(10) Patent No.: US 9,428,760 B2
(45) Date of Patent: Aug. 30, 2016

(54) OVEREXPRESSION OF STARCH SYNTHASE IN PLANTS

(71) Applicant: BAYER INTELLECTUAL PROPERTY GMBH, Monheim Am Rhein (DE)

(72) Inventors: Claus Frohberg, Kleinmachnow (DE); Ralf-Christian Schmidt, Stahnsdorf (DE)

(73) Assignee: BAYER INTELLECTUAL PROPERTY GMBH, Monheim Am Rhein (DE)

( * ) Notice: Subject to any disclaimer, the term of this patent is extended or adjusted under 35 U.S.C. 154(b) by 305 days.

(21) Appl. No.: 13/657,661

(22) Filed: Oct. 22, 2012

(65) Prior Publication Data

US 2013/0117894 A1 May 9, 2013

Related U.S. Application Data

(62) Division of application No. 11/996,061, filed as application No. PCT/EP2006/007389 on Jul. 24, 2006, now abandoned.

(60) Provisional application No. 60/701,764, filed on Jul. 22, 2005, provisional application No. 60/757,216, filed on Jan. 6, 2006, provisional application No. 60/757,810, filed on Jan. 10, 2006.

(30) Foreign Application Priority Data

Jul. 22, 2005 (EP) .................................. 05090220
Dec. 23, 2005 (EP) .................................. 05090349
Jan. 6, 2006 (EP) .................................. 06090003

(51) Int. Cl.
*C12N 15/82* (2006.01)
*C12N 9/12* (2006.01)
*C12N 9/10* (2006.01)

(52) U.S. Cl.
CPC ......... *C12N 15/8245* (2013.01); *C12N 9/1051* (2013.01)

(58) Field of Classification Search
CPC ............ C12N 15/8245; C12N 9/1051; C12N 9/1048; C12N 15/00; C12N 15/09
See application file for complete search history.

(56) References Cited

U.S. PATENT DOCUMENTS 6,307,125 B1 * 10/2001 Block et al. .................. 800/284
6,423,886 B1    7/2002 Singletary et al.
6,570,008 B1    5/2003 Broglie

FOREIGN PATENT DOCUMENTS

| WO | WO 97/45545 | 12/1997 |
| WO | WO 00/66745 | 11/2000 |
| WO | WO 02/079410 | 10/2002 |

OTHER PUBLICATIONS

Cornejo et al 1993 Plant Molecular Biology 23:567-581.*
Lim et al., "Location of Phosphate Esters in a Wheat Starch Phosphate by P(31)-Nuclear Magnetic Resonance Spectroscopy", Cereal Chem. (1993), vol. 70, No. 2, pp. 145-152.
Ritte et al., "Phosphorylation of C6- and C3-positions of glucosyl residues in starch is catalysed by distinct dikinases", FEBS Letters (2006), vol. 580, pp. 4872-4876.
Abel, et al., Cloning and functional analysis of a cDNA encoding a novel 139 kDa starch synthase from potato (*Solanum tuberosum* L.), Plant Journal, 10/(6):981-990, 1996.
Anderson, et al., Nucleotide sequences of the two high-molecular-weight glutenin genes from the D-genome of a hexaploid bread wheat, *Triticum aestivum* L. cv Cheyenne, Nuc. Acids Res., 17(1):461-462, 1989.
Accession No. A93354 (Jan. 22, 2000) "Nucleic Acid Molecules Encoding Enzymes from Wheat which are involved in Starch Synthesis."
Accession No. AAC86412 (Mar. 1, 2001) "Wheat Starch Synthase II Coding Sequence SEQ ID No. 5."
Baba, et al., Identification, cDNA Cloning, and Gene Expression of Soluble Starch Synthase in Rice (*Oryza sativa* L.) Immature Seeds, Plant Physiol., 103:565-573, 1993.
Bäumlein, et al., A novel seed protein gene from Vicia faba is developmentally regulated in transgenic tobacco and Arabidopsis plants, Mol. Gen. Genet., 225:459-467, 1991.
Blennow, et al., The distribution of covalently bound phosphate in the starch granule in relation to starch crystallinity, Int. J. of Bio. Macromol., 27:211-218, 2000.
Chaiwanichshiri, et al. (Dec. 2001) "Measurement of Electrical Conducitivity, differential Scanning Calorimetry and Viscosity of Starch and Flour Suspensions during gelantinisation process." Journal of the Science of Food and Agriculture 81(15): 1586-1591.
Champagne, et al. (1998) "Effects of Postharvest Processing on Texture Profile Analysis of Cooked Rice." Cereal Chem. 75(2): 181-186.
Chan, et al., Agrobacterium-mediated production of transgenic rice plants expressing a chimeric α-amylase promotor/ β -glucuronidase gene, Plant Mol. Bio., 22:491-506, 1993.
Conner, et al., Monocotyledonous Plants as Hosts for *Agrobacterium*, Int. J. Plant Sci., 153(4):550-555, 1992.
Deng, et al., *Agrobacterium tumefaciens* Can Transform *Triticum aestivum* and *Hordeum vulgare* of Gramineae, Sci. in China, 33(1):28-34, 1990.
Denyer, et al., Soluble isoforms of starch synthase and starch-branching enzyme also occur within starch granules in developing pea embryos, Plant Journal, 4(1):191-198, 1993.

(Continued)

Primary Examiner — Brent T Page
(74) Attorney, Agent, or Firm — Arent Fox LLP

(57) ABSTRACT

The present invention relates to a process for increasing the phosphate content of starches of genetically modified plant cells in comparison with starches from corresponding wild-type plant cells by introducing a foreign nucleic acid molecule which codes for a soluble starch synthase II. The present invention furthermore relates to the overexpression of this soluble starch synthase II in the genetically modified plant cells. Furthermore, the present invention relates to rice starch and rice flour with improved quality characteristics, to rice grains comprising this rice starch, and to rice plants on which these rice grains grow.

37 Claims, 3 Drawing Sheets

(56) References Cited

OTHER PUBLICATIONS

Dry, et al., Characterization of cDNAs encoding two isoforms of granule-bound starch synthase which show differential expression in developing storage organs of pea and potato, Plant Journal, 2(2):193-202, 1992.
Edwards, et al., Biochemical and molecular characterization of a novel starch synthase from potato tubers, Plant Journal, 8(2):283-294, 1995.
EMBL Accession No. AL021713 *Arabidopsis thaliana* DNA chromosome 4 BAC clone T9A21 (ESSA project) (Feb. 3, 1998).
Englyst, et al. (1992) "Classification and measurement of nutritionally important starch fractions." European J. of Clin. Nutirition 46(2): S33-S50.
Fitzgerald, et al., Viscosity of Rice Flour: A Rheological and Biological Study, J. Agric. Food Chem., 51:2295-2299, 2003.
Gao, et al., Characterization of *dull1*, a Maise Gene Coding for a Novel Starch Synthase, Plant Cell, 10:399-412, 1998.
Genbank Accession No. U66377, *Triticum aestivum* starch synthase mRNA, partial cds., 1996.
Genbank Accession No. AJ225088, Vigna unguiculata starch synthase isoform SS III, PLN Apr. 1, 1999, 2 pgs.
Genbank Accession No. AY044844, *Triticum aestivum* starch synthase isoform IV mRNA, complete cds; nuclear gene for plastid product, PLN Sep. 21, 2001, 2 pgs.
Harn, et al., Isolation and characterization of the zSSIIa and zSSIIb starch synthase cDNA clones from maize endosperm, Plant Mol. Bio., 37:639-649, 1998.
Have, "Hoffmann Mudra Plarre Lehrbuch der Züchtung landw"; *Kultulpflanen* (Textbook of the Breeding of Agricultural Useful Plants) 2: 110-123 (1985).
Hiei, et al., Efficient transformation of rice (*Oryza sativa* L.) mediated by *Agrobacterium* and sequence analysis of the boundaries of the T-DNA, Plant Journal, 6(2):271-282, 1994.
Ishida, et al., High efficiency transformation of maize (*Zea mays* L.) mediated by *Agrobacterium tumefaciens*, Nat. Biotech., 14(6):745-750, 1996.
Jane, et al., Phosphorus in Rice and Other Starches, Cereal Foods World, 41(11):827-832, 1996.
Jobling, et al., A minor form of starch branching enzyme in potato (*Solanum tuberosum* L.) tubers has a major effect on starch structure: cloning and characterisation of multiple forms of *SBE A*, Plant Journal, 18(2):163-171, 1999.
Juliano, et al. (1984) "International Cooperative Test on Texture of Cooked Rice." J of Texture Studies 15: 357-376.
Kawagoe, et al., Four distinct nuclear proteins recognize in vitro the proximal promoter of the bean seed storage protein β-phaseolin gene conferring spatial and temporal control, Plant J., 2(6):927-936, 1992.
Klösgen, et al., Molecular analysis of the *waxy* locus of *Zea mays*, Mol. Gen. Genet., 203:237-244, 1986.
Knight, et al., Molecular cloning of starch synthase I from maize (W64) endosperm and expression in *Escherichia coli*, Plant Journal, 14(5):613-622, 1998.
Kossmann and Lloyd (May 2000) "Understanding and Influencing Starch Biochemistry." Critical Reviews in Plant Sciences 19(3): 171-226.
Kossmann, et al., Cloning and expression analysis of a potato cDNA that encodes branching enzyme: evidence for co-expression of starch biosynthetic genes, Mol. Gen. Genet., 230:39-44, 1991.
Koziel, et al., Field Performance of Elite Transgenic Maize Plants Expressing an Insecticidal protein Derived from *Bacillus thuringiensis*, Bio/Technology, 11:194-200, 1993.
Leisy, et al., Expression of a rice glutelin promotor in transgenic tobacco, Plant Mol. Bio., 14:41-50, 1989.
Li, et al., The structural organisation of the gene encoding class II starch synthase of wheat and barley and the evolution of the genes encoding starch synthases in plants, Funct. Integr., Genomics, 3:76-85, 2003.
Lorberth, et al., Inhibition of a starch-granule-bound protein leads to modified starch amd expression and repression of cold sweetening, Nature Biotechnology, 16:473-477, 1998.
May, et al., Generation of Transgenic Banana (*Musa acuminata*) Plants via *Agrobacterium*-Mediated Transformation, Bio/Technology, 13:486-492, 1995.
Nakamura, Towards a Better Understanding of the Metabolic System for Amylopectin Biosynthesis in Plants: Rice Endosperm as a Model Tissue, Plant Cell Physiol. 43(7):718-725, 2002.
Nakamura, et al., Essential amino acids of starch synthase IIa differentiate amylopectin structure and starch quality between *japonica* and *indica* rice varieties, Plant Mol. Bio., 58:213-227, 2005.
Nakase, et al., Cloning of the rice seed a-globulin-encoding gene: sequence similarity of the 5'-flanking region to those of the genes encoding wheat high-molecular-weight glutenin and barley D hordein, Gene, 170: 223-226, 1996.
Nehra, et al., Self-fertile transgenic wheat plants regenerated from isolated scutellar tissues following microprojectile bombardment with two distinct gene constructs, Plant J., 5(2):285-297, 1994.
Nielsen, et al., Starch Phosphorylation in Potato Tubers Proceeds Concurrently with de Novo Biosynthesis of Starch, Plant Physiol., 105:111-117, 1994.
Okagaki, Nucleotide sequence of a long cDNA from the rice *waxy* gene; Plant Mol. Bio., 19:513-516, 1992.
Orthoefer, Corn Starch Modification and Uses, Corn: Chemistry and Technology, Chp. 16, pp. 479-499, 1987.
Patindol, et al., Fine Structures and Physicochemical Properties of Starches from Chalky and Translucent Rice Kernels, J. Agric. Food Chem., 51:2777-2784, 2003.
Pedersen, et al., Cloning and Sequence Analysis Reveal Structural Variation among Related Zein Genes in Maize, Cell, 29:1015-1026, 1982.
Ponstein, et al., Selective Measurement of Starch Synthesizing Enzymes in Permeabilized Potato Tuber Slices, Plant Physiol, 92: 234-241, 1990.
Qu, et al., Evaluation of tissue specificity and expression strength of rice seed component gene promoters in transgenic rice, Plant Biotech. J., 2:113-125, 2004.
Quattrocchio, et al., the maize zein gene zE19 contains two distinct promoters which are independently activated in endosperm and anthers of transgenic *Petunia* plants, Plant Mol. Bio., 15:81-88, 1990.
Ramesh, et al., Structure of rice starch and its relation to cooked-rice texture, Carbohydrate Polymers, 38:337-347, 1999.
Ritala, et al., Fertile transgenic barley by particle bombardment of immature embryos, Plant Mol. Bio., 24: 317-325, 1994.
Ritchie, et al., *Agrobacterium tumefaciens*-mediated expression of *gusA* in maize tissues, Transgenic Research, 2:252-265, 1993.
Safford, et al., Consequences of antisense RNA inhibition of starch branching enzyme activity on properties of potato starch, Carbohydrate Polymers, 35: 155-168, 1998.
Spencer, et al., Bialaphos selection of stable transformants from maize cell culture, Theor. Appl. Genet., 79:625-631, 1990.
Vandeputte et al., Journal of Cereal Science, vol. 38, pp. 43-52 (2003).
Van Der Leij, et al., Sequence of the structural gene for granule-bound starch synthase of potato (*Solanum tuberosum* L.) and evidence for a single point deletion in the *amf* allele, Mol. Gen. Genet., 228:240-248, 1991.
Vasil, et al. Rapid Production of Transgenic Wheat Plants by Direct Bombardment of Cultured Immature Embryos, Bio/Technology, 11: 1553-1558, 1993.
Wan, et al., Generation of large Numbers of Independently Transformed Fertile Barley Plants, Plant Physiol., 104:37-48, 1994.
Wang, et al., Rice starch isolation by neutral protease and high-intensity ultrasound, J. of Cereal Sci., 39:291-296, 2004.
Werr, et al., Structure of the sucrose synthase gene on chromosome 9 of *Zea mays* L., EMBO J., 4(6):1373-1380, 1985.

(56) References Cited

OTHER PUBLICATIONS

Wilmink, et al., Expression of the GUS-gene in the monocot tulip after introduction by particle bombardment and *Agrobacterium*, Plant Cell Rpts., 11: 76-80, 1992.

Wisker; "Resistente Starke: Ein Ballaststoff Komrnt in Mode" (Resistant Starch: A Dietary Febre is Getting Popular); UGB Forum; pp. 75-77; 2001.

Yamamoto, et al., Large-scale EST sequencing in rice, Plant Mol. Bio., 35:135-144, 1997.

Zheng, et al., 5' distal and proximal cis-acting regulator elements are required for developmental control of a rice seed storage protein *glutelin* gene, Plant J., 4(2):357-366, 1993.

* cited by examiner

SEQUENCE LISTING

```
<160> NUMBER OF SEQ ID NOS: 5

<210> SEQ ID NO 1
<211> LENGTH: 3006
<212> TYPE: DNA
<213> ORGANISM: Triticum aestivum
<220> FEATURE:
<221> NAME/KEY: CDS
<222> LOCATION: (227)..(2623)
<223> OTHER INFORMATION: Coding region
<220> FEATURE:
<221> NAME/KEY: Domain
<222> LOCATION: (1190)..(1279)
<223> OTHER INFORMATION: Region 1
<220> FEATURE:
<221> NAME/KEY: Domain
<222> LOCATION: (1493)..(1612)
<223> OTHER INFORMATION: Region 2
<220> FEATURE:
<221> NAME/KEY: Domain
<222> LOCATION: (2147)..(2350)
<223> OTHER INFORMATION: Region 3
<300> PUBLICATION INFORMATION:
<302> TITLE: Nucleic acid molecules encoding enzymes from wheat which
      are involved in starch synthesis
<308> DATABASE ACCESSION NUMBER: Derwent/AAV01528
<309> DATABASE ENTRY DATE: 1998-05-21
<310> PATENT DOCUMENT NUMBER: wo 97 45545
<311> PATENT FILING DATE: 1997-05-28
<312> PUBLICATION DATE: 1997-12-04
<313> RELEVANT RESIDUES IN SEQ ID NO: (1)..(2825)

<400> SEQUENCE: 1
ctccaccgcg gtggcggccg ctctagaact agtggatccc ccgggctgca ggaattcggc      60
acgagcttcg gcctgacccc gttcgtttac ccccacacag agcacactcc agtccagtcc     120
agcccactgc caccgcgcta ctctccactc ccactgccac cacctccgcc tgcgccgcgc     180
tctgggcgga ccaacccgcg aaccgtacca tctcccgccc cgatcc atg tcg tcg         235
                                                    Met Ser Ser
                                                     1 gcg gtc gcg tcc gcc gca tcc ttc ctc gcg ctc gcg tca gcc tcc ccc        283
Ala Val Ala Ser Ala Ala Ser Phe Leu Ala Leu Ala Ser Ala Ser Pro
      5                  10                  15 ggg aga tca cgc agg cgg gcg agg gtg agc gcg cag cca ccc cac gcc        331
Gly Arg Ser Arg Arg Ala Arg Val Ser Ala Gln Pro Pro His Ala
 20                  25                  30                  35 ggg gcc ggc agg ttg cac tgg ccg ccg tgg ccg ccg cag cgc acg gct        379
Gly Ala Gly Arg Leu His Trp Pro Pro Trp Pro Pro Gln Arg Thr Ala
                  40                  45                  50 cgc gac gga gct gtg gcg gcg ctc gcc gcc ggg aag aag gac gcg ggg        427
Arg Asp Gly Ala Val Ala Ala Leu Ala Ala Gly Lys Lys Asp Ala Gly
              55                  60                  65 atc gac gac gcc gcc gcg tcc gtg agg cag ccc cgc gca ctc cgc ggt        475
Ile Asp Asp Ala Ala Ala Ser Val Arg Gln Pro Arg Ala Leu Arg Gly
          70                  75                  80
```

-continued

| | | |
|---|---|---|
| ggc gcc gcc acc aag gtc gcg gag cga agg gat ccc gtc aag acg ctc<br>Gly Ala Ala Thr Lys Val Ala Glu Arg Arg Asp Pro Val Lys Thr Leu<br>85           90              95 | 523 |
| gac cgc gac gcc gcg gaa ggc ggc ggg ccg tcc ccg ccg gca gcg agg<br>Asp Arg Asp Ala Ala Glu Gly Gly Gly Pro Ser Pro Pro Ala Ala Arg<br>100             105                110              115 | 571 |
| cag gac gcc gcc cgt ccg ccg agt atg aac ggc atg ccg gtg aac ggc<br>Gln Asp Ala Ala Arg Pro Pro Ser Met Asn Gly Met Pro Val Asn Gly<br>         120              125              130 | 619 |
| gag aac aaa tct acc ggc ggc ggc gcg act aaa gac agc ggg ctg<br>Glu Asn Lys Ser Thr Gly Gly Gly Ala Thr Lys Asp Ser Gly Leu<br>         135              140              145 | 667 |
| ccc acg ccc gca cgc gcg ccc cat ccg tcg acc cag aac aga gca ccg<br>Pro Thr Pro Ala Arg Ala Pro His Pro Ser Thr Gln Asn Arg Ala Pro<br>         150              155              160 | 715 |
| gtg aac ggt gaa aac aaa gct aac gtc gcc tcg ccg ccg acg agc ata<br>Val Asn Gly Glu Asn Lys Ala Asn Val Ala Ser Pro Pro Thr Ser Ile<br>165             170              175 | 763 |
| gcc gag gcc gcg gct tcg gat tcc gca gct acc att tcc atc agc gac<br>Ala Glu Ala Ala Ala Ser Asp Ser Ala Ala Thr Ile Ser Ile Ser Asp<br>180             185              190              195 | 811 |
| aag gcg ccg gag tcc gtt gtc cca gct gag aag acg ccg ccg tcg tcc<br>Lys Ala Pro Glu Ser Val Val Pro Ala Glu Lys Thr Pro Pro Ser Ser<br>              200              205              210 | 859 |
| ggc tca aat ttc gag tcc tcg gcc tct gct ccc ggg tct gac act gtc<br>Gly Ser Asn Phe Glu Ser Ser Ala Ser Ala Pro Gly Ser Asp Thr Val<br>         215              220              225 | 907 |
| agc gac gtg gaa caa gaa ctg aag aag ggt gcg gtc gtt gtc gaa gaa<br>Ser Asp Val Glu Gln Glu Leu Lys Lys Gly Ala Val Val Val Glu Glu<br>         230              235              240 | 955 |
| gct cca aag cca aag gct ctt tcg ccg cct gca gcc ccc gct gta caa<br>Ala Pro Lys Pro Lys Ala Leu Ser Pro Pro Ala Ala Pro Ala Val Gln<br>245             250              255 | 1003 |
| gaa gac ctt tgg gat ttc aag aaa tac att ggt ttc gag gag ccc gtg<br>Glu Asp Leu Trp Asp Phe Lys Lys Tyr Ile Gly Phe Glu Glu Pro Val<br>260             265              270              275 | 1051 |
| gag gcc aag gat gat ggc cgg gct gtc gca gat gat gcg ggc tcc ttt<br>Glu Ala Lys Asp Asp Gly Arg Ala Val Ala Asp Asp Ala Gly Ser Phe<br>              280              285              290 | 1099 |
| gaa cac cac cag aat cac gac tcc gga cct ttg gca ggg gag aat gtc<br>Glu His His Gln Asn His Asp Ser Gly Pro Leu Ala Gly Glu Asn Val<br>         295              300              305 | 1147 |
| atg aac gtg gtc gtc gtg gct gct gag tgt tct ccc tgg tgc aaa aca<br>Met Asn Val Val Val Val Ala Ala Glu Cys Ser Pro Trp Cys Lys Thr<br>         310              315              320 | 1195 |
| ggt ggt ctg gga gat gtt gcg ggt gct ctg ccc aag gct ttg gca aag<br>Gly Gly Leu Gly Asp Val Ala Gly Ala Leu Pro Lys Ala Leu Ala Lys<br>         325              330              335 | 1243 |
| aga gga cat cgt gtt atg gtt gtg gta cca agg tat ggg gac tat gaa<br>Arg Gly His Arg Val Met Val Val Pro Arg Tyr Gly Asp Tyr Glu<br>340             345              350              355 | 1291 |
| gaa gcc tac gat gtc gga gtc cga aaa tac tac aag gct gct gga cag<br>Glu Ala Tyr Asp Val Gly Val Arg Lys Tyr Tyr Lys Ala Ala Gly Gln<br>              360              365              370 | 1339 |
| gat atg gaa gtg aat tat ttc cat gct tat atc gat gga gtt gat ttt<br>Asp Met Glu Val Asn Tyr Phe His Ala Tyr Ile Asp Gly Val Asp Phe<br>         375              380              385 | 1387 |
| gtg ttc att gac gct cct ctc ttc cga cac cgt cag gaa gac att tat<br>Val Phe Ile Asp Ala Pro Leu Phe Arg His Arg Gln Glu Asp Ile Tyr<br>         390              395              400 | 1435 |

```
ggg ggc agc aga cag gaa att atg aag cgc atg att ttg ttc tgc aag    1483
Gly Gly Ser Arg Gln Glu Ile Met Lys Arg Met Ile Leu Phe Cys Lys
    405                 410                 415 gcc gct gtt gag gtt cca tgg cac gtt cca tgc ggc ggt gtc cct tat    1531
Ala Ala Val Glu Val Pro Trp His Val Pro Cys Gly Gly Val Pro Tyr
420                 425                 430                 435 ggg gat gga aat ctg gtg ttt att gca aat gat tgg cac acg gca ctc    1579
Gly Asp Gly Asn Leu Val Phe Ile Ala Asn Asp Trp His Thr Ala Leu
                440                 445                 450 ctg cct gtc tat ctg aaa gca tat tac agg gac cat ggt ttg atg cag    1627
Leu Pro Val Tyr Leu Lys Ala Tyr Tyr Arg Asp His Gly Leu Met Gln
            455                 460                 465 tac act cgg tcc att atg gtg ata cat aac atc gct cac cag ggc cgt    1675
Tyr Thr Arg Ser Ile Met Val Ile His Asn Ile Ala His Gln Gly Arg
        470                 475                 480 ggc cct gta gat gaa ttc ccg ttc acc gag ttg cct gag cac tac ctg    1723
Gly Pro Val Asp Glu Phe Pro Phe Thr Glu Leu Pro Glu His Tyr Leu
    485                 490                 495 gaa cac ttc aga ctg tac gac ccc gtg ggt ggt gaa cac gcc aac tac    1771
Glu His Phe Arg Leu Tyr Asp Pro Val Gly Gly Glu His Ala Asn Tyr
500                 505                 510                 515 ttc gcc gcc ggc ctg aag atg gcg gac cag gtt gtc gtg gtg agc ccc    1819
Phe Ala Ala Gly Leu Lys Met Ala Asp Gln Val Val Val Val Ser Pro
                520                 525                 530 ggg tac ctg tgg gag ctg aag acg gtg gag ggc ggc tgg ggg ctt cac    1867
Gly Tyr Leu Trp Glu Leu Lys Thr Val Glu Gly Gly Trp Gly Leu His
            535                 540                 545 gac atc ata cgg cag aac gac tgg aag acc cgc ggc atc gtc aac ggc    1915
Asp Ile Ile Arg Gln Asn Asp Trp Lys Thr Arg Gly Ile Val Asn Gly
        550                 555                 560 atc gac aac atg gag tgg aac ccc gag gtg gac gcc cac ctc aag tcg    1963
Ile Asp Asn Met Glu Trp Asn Pro Glu Val Asp Ala His Leu Lys Ser
    565                 570                 575 gac ggc tac acc aac ttc tcc ctg agg acg ctg gac tcc ggc aag cgg    2011
Asp Gly Tyr Thr Asn Phe Ser Leu Arg Thr Leu Asp Ser Gly Lys Arg
580                 585                 590                 595 cag tgc aag gag gcc ctg cag cgc gag ctg ggc ctg cag gtc cgc gcc    2059
Gln Cys Lys Glu Ala Leu Gln Arg Glu Leu Gly Leu Gln Val Arg Ala
                600                 605                 610 gac gtg ccg ctg ctc ggc ttc atc ggc cgc ctg gac ggg cag aag ggc    2107
Asp Val Pro Leu Leu Gly Phe Ile Gly Arg Leu Asp Gly Gln Lys Gly
            615                 620                 625 gtg gag atc atc gcg gac gcc atg ccc tgg atc gtg agc cag gac gtg    2155
Val Glu Ile Ile Ala Asp Ala Met Pro Trp Ile Val Ser Gln Asp Val
        630                 635                 640 cag ctg gtg atg ctg ggc acc ggg cgc cac gac ctg gag agc atg ctg    2203
Gln Leu Val Met Leu Gly Thr Gly Arg His Asp Leu Glu Ser Met Leu
    645                 650                 655 cag cac ttc gag cgg gag cac cac gac aag gtg cgc ggg tgg gtg ggg    2251
Gln His Phe Glu Arg Glu His His Asp Lys Val Arg Gly Trp Val Gly
660                 665                 670                 675 ttc tcc gtg cgc ctg gcg cac cgg atc acg gcg ggg gcg gac gcg ctc    2299
Phe Ser Val Arg Leu Ala His Arg Ile Thr Ala Gly Ala Asp Ala Leu
                680                 685                 690 ctc atg ccc tcc cgg ttc gag ccg tgc ggg ctg aac cag ctc tac gcc    2347
Leu Met Pro Ser Arg Phe Glu Pro Cys Gly Leu Asn Gln Leu Tyr Ala
            695                 700                 705 atg gcc tac ggc acc gtc ccc gtc gtg cac gcc gtc ggc ggc ctc agg    2395
Met Ala Tyr Gly Thr Val Pro Val Val His Ala Val Gly Gly Leu Arg
```

```
              710                 715                 720
gac acc gtg ccg ccg ttc gac ccc ttc aac cac tcc ggg ctc ggg tgg   2443
Asp Thr Val Pro Pro Phe Asp Pro Phe Asn His Ser Gly Leu Gly Trp
    725                 730                 735 acg ttc gac cgc gcc gag gcg cac aag ctg atc gag gcg ctc ggg cac   2491
Thr Phe Asp Arg Ala Glu Ala His Lys Leu Ile Glu Ala Leu Gly His
740                 745                 750                 755 tgc ctc cgc acc tac cga gac ttc aag gag agc tgg agg gcc ctc cag   2539
Cys Leu Arg Thr Tyr Arg Asp Phe Lys Glu Ser Trp Arg Ala Leu Gln
                760                 765                 770 gag cgc ggc atg tcg cag gac ttc agc tgg gag cac gcc gcc aag ctc   2587
Glu Arg Gly Met Ser Gln Asp Phe Ser Trp Glu His Ala Ala Lys Leu
            775                 780                 785 tac gag gac gtc ctc gtc aag gcc aag tac cag tgg tgaacgctag        2633
Tyr Glu Asp Val Leu Val Lys Ala Lys Tyr Gln Trp
        790                 795 ctgctagccg ctccagcccc gcatgcgtgc atgacaggat ggaactgcat tgcgcacgca  2693
ggaaagtgcc atggagcgcc ggcatccgcg aagtacagtg acatgaggtg tgtgtggttg  2753
agacgctgat tccaatccgg cccgtagcag agtagagcgg aggtatatgg gaatcttaac  2813
ttggtattgt aatttgttat gttgtgtgca ttattacaat gttgttactt attcttgtta  2873
agtcggaggc caagggcgaa agctagctca catgtctgat ggatgcacgt gccatggttg  2933
gtttggtagc gcagtgcaaa cggcaagaat gggaagtgaa ttcctccctg cttgaaaaaa  2993
aaaaaaaaaa aaa                                                    3006

<210> SEQ ID NO 2
<211> LENGTH: 799
<212> TYPE: PRT
<213> ORGANISM: Triticum aestivum

<400> SEQUENCE: 2

Met Ser Ser Ala Val Ala Ser Ala Ala Ser Phe Leu Ala Leu Ala Ser
1               5                   10                  15

Ala Ser Pro Gly Arg Ser Arg Arg Ala Arg Val Ser Ala Gln Pro
                20                  25                  30

Pro His Ala Gly Ala Gly Arg Leu His Trp Pro Pro Trp Pro Pro Gln
            35                  40                  45

Arg Thr Ala Arg Asp Gly Ala Val Ala Ala Leu Ala Ala Gly Lys Lys
    50                  55                  60

Asp Ala Gly Ile Asp Asp Ala Ala Ala Ser Val Arg Gln Pro Arg Ala
65                  70                  75                  80

Leu Arg Gly Gly Ala Ala Thr Lys Val Ala Glu Arg Arg Asp Pro Val
                85                  90                  95

Lys Thr Leu Asp Arg Asp Ala Ala Glu Gly Gly Pro Ser Pro
                100                 105                 110

Ala Ala Arg Gln Asp Ala Ala Arg Pro Pro Ser Met Asn Gly Met Pro
            115                 120                 125

Val Asn Gly Glu Asn Lys Ser Thr Gly Gly Gly Ala Thr Lys Asp
    130                 135                 140

Ser Gly Leu Pro Thr Pro Ala Arg Ala Pro His Pro Ser Thr Gln Asn
145                 150                 155                 160

Arg Ala Pro Val Asn Gly Glu Asn Lys Ala Asn Val Ala Ser Pro Pro
                165                 170                 175

Thr Ser Ile Ala Glu Ala Ala Ala Ser Asp Ser Ala Ala Thr Ile Ser
            180                 185                 190
```

```
Ile Ser Asp Lys Ala Pro Glu Ser Val Val Pro Ala Glu Lys Thr Pro
        195                 200                 205

Pro Ser Ser Gly Ser Asn Phe Glu Ser Ser Ala Ser Ala Pro Gly Ser
    210                 215                 220

Asp Thr Val Ser Asp Val Glu Gln Glu Leu Lys Lys Gly Ala Val Val
225                 230                 235                 240

Val Glu Glu Ala Pro Lys Pro Lys Ala Leu Ser Pro Pro Ala Ala Pro
                245                 250                 255

Ala Val Gln Glu Asp Leu Trp Asp Phe Lys Lys Tyr Ile Gly Phe Glu
            260                 265                 270

Glu Pro Val Glu Ala Lys Asp Asp Gly Arg Ala Val Ala Asp Asp Ala
        275                 280                 285

Gly Ser Phe Glu His His Gln Asn His Asp Ser Gly Pro Leu Ala Gly
    290                 295                 300

Glu Asn Val Met Asn Val Val Val Ala Ala Glu Cys Ser Pro Trp
305                 310                 315                 320

Cys Lys Thr Gly Gly Leu Gly Asp Val Ala Gly Ala Leu Pro Lys Ala
                325                 330                 335

Leu Ala Lys Arg Gly His Arg Val Met Val Val Val Pro Arg Tyr Gly
            340                 345                 350

Asp Tyr Glu Glu Ala Tyr Asp Val Gly Val Arg Lys Tyr Tyr Lys Ala
        355                 360                 365

Ala Gly Gln Asp Met Glu Val Asn Tyr Phe His Ala Tyr Ile Asp Gly
    370                 375                 380

Val Asp Phe Val Phe Ile Asp Ala Pro Leu Phe Arg His Arg Gln Glu
385                 390                 395                 400

Asp Ile Tyr Gly Gly Ser Arg Gln Glu Ile Met Lys Arg Met Ile Leu
                405                 410                 415

Phe Cys Lys Ala Ala Val Glu Val Pro Trp His Val Pro Cys Gly Gly
            420                 425                 430

Val Pro Tyr Gly Asp Gly Asn Leu Val Phe Ile Ala Asn Asp Trp His
        435                 440                 445

Thr Ala Leu Leu Pro Val Tyr Leu Lys Ala Tyr Tyr Arg Asp His Gly
    450                 455                 460

Leu Met Gln Tyr Thr Arg Ser Ile Met Val Ile His Asn Ile Ala His
465                 470                 475                 480

Gln Gly Arg Gly Pro Val Asp Glu Phe Pro Phe Thr Glu Leu Pro Glu
                485                 490                 495

His Tyr Leu Glu His Phe Arg Leu Tyr Asp Pro Val Gly Gly Glu His
            500                 505                 510

Ala Asn Tyr Phe Ala Ala Gly Leu Lys Met Ala Asp Gln Val Val Val
        515                 520                 525

Val Ser Pro Gly Tyr Leu Trp Glu Leu Lys Thr Val Glu Gly Gly Trp
    530                 535                 540

Gly Leu His Asp Ile Ile Arg Gln Asn Asp Trp Lys Thr Arg Gly Ile
545                 550                 555                 560

Val Asn Gly Ile Asp Asn Met Glu Trp Asn Pro Glu Val Asp Ala His
                565                 570                 575

Leu Lys Ser Asp Gly Tyr Thr Asn Phe Ser Leu Arg Thr Leu Asp Ser
            580                 585                 590

Gly Lys Arg Gln Cys Lys Glu Ala Leu Gln Arg Glu Leu Gly Leu Gln
        595                 600                 605
```

```
Val Arg Ala Asp Val Pro Leu Leu Gly Phe Ile Gly Arg Leu Asp Gly
    610                 615                 620

Gln Lys Gly Val Glu Ile Ile Ala Asp Ala Met Pro Trp Ile Val Ser
625                 630                 635                 640

Gln Asp Val Gln Leu Val Met Leu Gly Thr Gly Arg His Asp Leu Glu
                645                 650                 655

Ser Met Leu Gln His Phe Glu Arg Glu His His Asp Lys Val Arg Gly
            660                 665                 670

Trp Val Gly Phe Ser Val Arg Leu Ala His Arg Ile Thr Ala Gly Ala
        675                 680                 685

Asp Ala Leu Leu Met Pro Ser Arg Phe Glu Pro Cys Gly Leu Asn Gln
690                 695                 700

Leu Tyr Ala Met Ala Tyr Gly Thr Val Pro Val Val His Ala Val Gly
705                 710                 715                 720

Gly Leu Arg Asp Thr Val Pro Pro Phe Asp Pro Phe Asn His Ser Gly
                725                 730                 735

Leu Gly Trp Thr Phe Asp Arg Ala Glu Ala His Lys Leu Ile Glu Ala
            740                 745                 750

Leu Gly His Cys Leu Arg Thr Tyr Arg Asp Phe Lys Glu Ser Trp Arg
        755                 760                 765

Ala Leu Gln Glu Arg Gly Met Ser Gln Asp Phe Ser Trp Glu His Ala
770                 775                 780

Ala Lys Leu Tyr Glu Asp Val Leu Val Lys Ala Lys Tyr Gln Trp
785                 790                 795

<210> SEQ ID NO 3
<211> LENGTH: 30
<212> TYPE: PRT
<213> ORGANISM: Triticum aestivum

<400> SEQUENCE: 3

Lys Thr Gly Gly Leu Gly Asp Val Ala Gly Ala Leu Pro Lys Ala Leu
1               5                   10                  15

Ala Lys Arg Gly His Arg Val Met Val Val Val Pro Arg Tyr
            20                  25                  30

<210> SEQ ID NO 4
<211> LENGTH: 40
<212> TYPE: PRT
<213> ORGANISM: Triticum aestivum

<400> SEQUENCE: 4

Glu Val Pro Trp His Val Pro Cys Gly Gly Val Pro Tyr Gly Asp Gly
1               5                   10                  15

Asn Leu Val Phe Ile Ala Asn Asp Trp His Thr Ala Leu Leu Pro Val
            20                  25                  30

Tyr Leu Lys Ala Tyr Tyr Arg Asp
        35                  40

<210> SEQ ID NO 5
<211> LENGTH: 68
<212> TYPE: PRT
<213> ORGANISM: Triticum aestivum

<400> SEQUENCE: 5

Gln Asp Val Gln Leu Val Met Leu Gly Thr Gly Arg His Asp Leu Glu
1               5                   10                  15

Ser Met Leu Gln His Phe Glu Arg Glu His His Asp Lys Val Arg Gly
```

```
                20                  25                  30
Trp Val Gly Phe Ser Val Arg Leu Ala His Arg Ile Thr Ala Gly Ala
            35                  40                  45

Asp Ala Leu Leu Met Pro Ser Arg Phe Glu Pro Cys Gly Leu Asn Gln
        50                  55                  60

Leu Tyr Ala Met
65
```

OVEREXPRESSION OF STARCH SYNTHASE IN PLANTS

CROSS-REFERENCE TO RELATED APPLICATIONS

This application is a Divisional Application of U.S. application Ser. No. 11/996,061, filed Sep. 11, 2008, which is a U.S. National Stage filing of International Application No. PCT/EP2006/007389, filed Jul. 24, 2006, which claims priority to U.S. Provisional Patent Application No. 60/701,764, filed Jul. 22, 2005, European Patent No. EP 05090220.4, filed Jul. 22, 2005, European Patent No. EP 05090349.1, filed Dec. 23, 2005, U.S. Provisional Patent Application No. 60/757,216 filed Jan. 6, 2006, European Patent No. EP 06090003.2, filed Jan. 6, 2006, and U.S. Provisional Patent Application No. 60/757,810 filed Jan. 10, 200, the disclosures of each of which are hereby incorporated by reference.

BACKGROUND OF THE INVENTION (i) Field of the Invention

The present invention relates to a process for increasing the phosphate content of starches of genetically modified plant cells in comparison with starches from corresponding genetically nonmodified wild-type plant cells, wherein a plant cell is genetically modified by the introduction of a foreign nucleic acid molecule which codes for a soluble starch synthase II, and this starch synthase II is overexpressed.

Furthermore, the present invention relates to rice starch and rice flour with improved quality properties, to rice grains comprising this rice starch, and the rice plants on which these rice grains grow.

(ii) Description of the Related Art

Rice is the most important food for more than half of the world's population. In some countries, rice amounts to approximately 80% of all the food intake. The annual production worldwide is 550 million tonnes of rice.

The rice kernel consists of approximately 76% of starch and approximately 7-8% of protein. It contains only 1.3% of fat and a large number of trace elements (0.6%) such as phosphorus, iron and magnesium.

The economically most important rice species is *Oryza sativa*, whose basic varieties can be divided into two groups: the "*indica*" group, which includes only long-grain rice, and the "*japonica*" group, which contains medium- and short-grain rice.

Long-grain rice (rice varieties whose grains are separate when cooked) comes mainly from India or Java; short-grain rice (such as "pudding rice", i.e. rice varieties whose grains are sticky when cooked) come primarily from Japan. The varieties from China and South East Asia are halfway between the above.

In all varieties, in turn, there are two main types: translucent grain or opaque grain. These differ in the composition of their starch: the starch of translucent rice consists of approximately 20% of amylose and to 80% of amylopectin, while that of the opaque rice, in contrast, consists virtually only of amylopectin.

Amylopectin has a specific cluster structure and is synthesized by a variety of subunits or isoforms of four classes of enzymes: soluble starch synthase (SS), starch-branching enzymes (SBE), starch-debranching enzymes (SDE) and ADP glucose pyrophosphorylase (Nakamura 2002, Plant Cell Physiol. 43(7): 718-725).

The cooking and eating characteristics are determined mostly by the amylose content of the rice endosperm. Varieties with a low amylose content are damp and sticky after cooking, while grains with a high amylose content go dry and fluffy upon cooking (H. ten Have in Hoffmann Mudra Plarre (HMP) 1985: Lehrbuch der Züchtung landw. Kulturpflanzen, Volume 2, pp. 110-123).

Grain quality is very important not only for the consumer, but also for the milling industry; grain properties such as grain size, grain shape and grain quality are important features since they affect the yield of ground rice and the percentage of broken grains (ten Have 1985, supra).

Rice flour is relatively neutral in taste and therefore very suitable as the basis for mild-tasting products or else as an admixture. Owing to its hypoallerginicity, it is also very suitable for baby formula or as diet for allergy sufferers.

Besides oils, fats and proteins, polysaccharides are the most important renewable raw materials from plants. Besides cellulose, starch, which is one of the most important storage materials in Higher Plants, is of prime importance among the polysaccharides.

The polysaccharide starch is a polymer of chemically uniform units, the glucose molecules. However, it constitutes a highly complex mixture of different forms of molecules which differ with regard to their degree of polymerization and the occurrence of branchings of the glucose chains and their chain length and, additionally, may be derivatized, for example phosphorylated. Starch therefore does not constitute a uniform raw material. In particular, amylose starch, an essentially unbranched polymer of α-1,4-glycosidically linked glucose molecules, differs from amylopectin starch, which, in turn, is a complex mixture of differently branched glucose chains. The branchings are formed by the occurrence of additional α-1,6-glycosidic linkages. In typical plants used for industrial starch production, for example maize, wheat or potato, the starch synthesized is approximately 20%-25% amylose starch and approximately 70%-75% amylopectin starch.

The functional properties of starch are affected greatly not only by the amylose/amylopectin ratio and the phosphate content, but also by the molecular weight, the pattern of the side-chain distribution, the ionic content, the lipid and protein content, the mean size of the starch grains, the starch grain morphology and the like. Important functional properties which may be mentioned in this context are, for example, the solubility, the retrogradation behavior, the water-binding capacity, the film-forming properties, the viscosity, the pasting properties, the freeze-thaw stability, the stability to acids, the gel strength and the like.

The basic biochemical synthetic pathways which lead to the synthesis of starch are only roughly known. However, there exists a series of steps in which the detailed mechanisms which lead to the synthesis of the starch granules and of the starch are hitherto not elucidated and therefore still the subject of research.

It is currently not possible to influence the content of covalently bonded starch phosphate in plants by means of plant breeding alone.

An alternative to plant breeding methods is the targeted modification of starch-producing plants by recombinant methods. The prerequisite herefor, however, is the identification and characterization of the enzymes which participate in starch synthesis and/or in the modification of starch, and the isolation of the nucleic acid molecules which code for these enzymes and the subsequent functional analysis in transgenic plants.

In plant cells, starch synthesis takes place in the plastids, which are the chloroplasts in photosynthetically active tissue and the amyloplasts in photosynthetically inactive, starch-storing tissue. Important enzymes which play a role in starch synthesis are the R1 proteins (=alpha-glucan water dikinase, E.C. 2.7.9.4; Lorberth et al. (1998) Nature Biotechnology 16: 473-477), starch synthases and the branching enzymes (=BE; see, for example, Ponstein et al., Plant Physiol. 29 (1990), 234-241; Kossmann et al., 1991, Mol. Gen. Genet. 230, 39-44; Safford et al., 1998, Carbohydrate Polymers 35, 155-168; Jobling et al. 1999, The Plant Journal 18(2): 163-171). Branching enzymes catalyze the introduction of α-1,6-branchings into linear α-1,4-glucans. In the starch synthases, a variety of isoforms have been described, all of which catalyze a polymerization reaction by transferring a glucosyl residue from ADP-glucose to α-1,4-glucans.

An overview over native starches isolated from various plant species, where variations of enzymes which play a role in starch biosynthesis are observed, can be found in Kossmann and Lloyd (2000, Critical Reviews in Plant Sciences 19(3): 171-226).

Starch synthases (EC 2.4.1.21) can be divided into two classes: the starch-granule-bound starch synthases ("granule-bound starch synthases I"; GBSS I) and the soluble starch synthase ("soluble starch synthases"; SSS, also referred to as "SS"). This distinction is not unambiguous in each case since some of the starch synthases exist both in starch-granule-bound form and in soluble form (Denyer et al., Plant J. 4 (1993), 191-198; Mu et al., Plant J. 6 (1994), 151-159).

In contrast to the GBSSI, which leads to the synthesis of amylose, little is known as yet about the precise enzymatic function of the various classes of soluble starch synthase in starch biosynthesis.

The biochemical characterization resulted in the identification of soluble starch synthase proteins with molecular weights of between approximately 60 to approximately 180 kDa. The cloning of cDNAs which code for starch synthases made it possible to distinguish different classes which were defined as the result of sequence homologies and as the result of the functional characteristics of the (soluble) starch synthases.

To date, eight classes of starch synthases have been identified in higher plants (inter alia by Li et al. (2003) Funct. Intergr. Genomics 3:76-85):

starch-granule-bound starch synthase I (Granule-Bound Starch Synthase I=GBSS I) (rice: for example Okagaki (1992) Plant Mol. Biol. 19:513-516; potato: van der Leij et al. (1991) Mol. Gen. Genet. 228:240-248; maize: for example Kloesgen et al. (1986) Mol. Gen. Genet. 203:237-244);

soluble starch synthase I (=SSI; rice: Baba et al. (1993) Plant Physiol. 103:565-573; potato: Kossmann et al. (1999) Planta 208: 503-511; maize: Knight et al. (1998) Plant J. 14:613-622);

soluble starch synthase II (=SSII; pea: Dry et al. (1992) Plant J. 2:193-202, potato: Edwards et al. (1995) Plant J 8: 283-294, maize: Harn et al, (1998) Plant Mol. Biol. 37(4): 639-649; wheat: Walter et al. (1996) Genbank Acc. U66377; rice: Yamamoto and Sasaki (1997) Plant Mol. Biol. 35:135-144 and barley: Li et al. (2003), Funct. Integr. Genomics 3: 76-85);

soluble starch synthase III (=SSIII; potato: Abel et al. (1996) Plant J 10:981-991: fodder pea: GenBank Acc. No AJ225088);

soluble starch synthase IV (=SSIV; wheat: GenBank Acc. No AY044844);

soluble starch synthase V (=SSV; fodder pea: GenBank Acc. No VUN006752; *Arabidopsis*: GenBank Acc. No AL021713; maize: WO 97/26362) and dull (Gao et al. (1998) Plant Cell 10:399-412;

soluble starch synthase VI (=SSVI; maize: WO 01/12826).

The content of covalently bound starch phosphate varies, depending on the plant species. Thus, for example, certain maize mutants synthetize starch with an increased starch phosphate content (waxy maize 0.002% and high-amylose maize 0.013%), while traditional maize varieties only contain traces of starch phosphate. Small amounts of starch phosphate are also found in wheat (0.001%), while no starch phosphate was detected in oats and millet. Likewise, less starch phosphate was found in rice mutants (waxy rice 0.003%) than in traditional rice varieties (0.013%). Significant amounts of starch phosphate were detected in plants which synthetize tuber- or root-reserve starch such as, for example, tapioca (0.008%), sweet potato (0.011%), arrowroot (0.021%) or potato (0.089%). These percentages for the starch phosphate content are in each case based on the dry weight of starch and have been determined by Jane et al. (1996, Cereal Foods World 41 (11), 827-832). Studies on SSI-antisense potatoes revealed that their phosphate content was increased by 30-70% over the wild type (WO 96/15248).

WO 00/08184 describes plants in which both the activities of starch synthase III (=SSIII) and of branching enzyme I (=BEI) are reduced. In comparison with starch from wild-type plants, starch from such plants has an elevated phosphate content. Wheat plants which, as the result of the overexpression of an R1 gene from potato, have an increased activity of an R1 protein and an increased starch phosphate content are described in the international patent application WO 02/34923.

The distribution of phosphate in starch which has been synthesized by plants (native starch) is generally distinguished by the fact that approximately 30% to 40% of the phosphate residues are bonded covalently in the C3 position and approximately 60% to 70% of the phosphate residues in the C6 position of the glucose molecules (Blennow et al., 2000, Int. J. of Biological Macromolecules 27: 211-218). In contrast, chemically phosphorylated starches additionally have phosphate residues bonded in the C2 position of the glucose molecules since the chemical reaction proceeds in an undirected fashion.

WO 03/023024 discloses rice starches which have a DSC T-onset temperature of up to 69.5° C. and/or a DSC T-peak temperature of up to 73.6° C.; a total of approximately 400 rice varieties of the groups *japonica* and *indica* have been analyzed for these features.

Umemoto et al. (2002, Theor. Appl. Genet. 104:1-8) describe the analysis of back-crossed inbred lines between a *japonica* variety (*Nipponbare*) and an *indica* variety (*Kasalath*). They conclude from their results that the alk(t), gel(t) and acl(t) locus, which is responsible for the different gelatinization onset temperatures (DSC T-onset) between *japonica* and *indica* varieties, might be the starch synthase isoform SSIIa.

WO 03/023024 describes a rice transformant (#78-1) of the *japonica* variety (*Kinmaze*) into which a gene of starch synthase IIa (SSIIa) from the *indica* form IR36 has been transformed. The resulting changes in the amylopectin side-chain profile are shown and, as a consequence, indicate a shift from the *japonica* profile towards that of the *indica* variety (FIG. 22 in WO 03/023024).

WO 03/023024 describes neither phosphate contents, amylose contents nor rheological properties of the rice starches or flours.

The relationship between the change in the amylopectin side-chain profile, which is brought about by SSIIa, and the DSC T-onset temperature of the starches is again shown, in a recently published paper (Nakamura et al., (2005) PMB; 58(2): 213-27), with reference to the values for the transformants and the corresponding "recipient" and "donor" lines (FIG. 6B). FIG. 6B shows the temperatures for DSC T-onset of the starches of the SSIIa-transformants generated. In no case is the DSC T-onset higher than 70° C. The highest T-onset value detailed therein is 69.5° C., as described also in WO 03/023024 (pp. 21-24).

Thus, neither WO 03/023024 nor Nakamura et al. (2005) teach a way in which rice starches whose DSC T-onset temperature exceeds 70° C. can be generated.

However, a higher DSC T-onset temperature is desired insofar as it is an important feature of an improved thermal stability of starches and thus also for the change in the crystalline structure as the result of the effect of heat.

SUMMARY OF EMBODIMENTS OF THE INVENTION

It was an object of the present invention therefore to provide rice starches and rice flours with new properties, in particular an improved thermal stability, and means and methods for their preparation.

How increasing the gene expression of the soluble starch synthase II affects the starch properties in plants was hitherto unknown. A high phosphate content is desired since it leads to modified physico-chemical characteristics of the starch and thus to novel applications of the starch.

It is therefore a further object of the present invention to provide a process by means of which the phosphate content of starches of plants can be increased in vivo.

These objectives are achieved by providing the use forms specified in the patent claims.

DETAILED DESCRIPTION OF EMBODIMENTS OF THE INVENTION

Figure 1A:
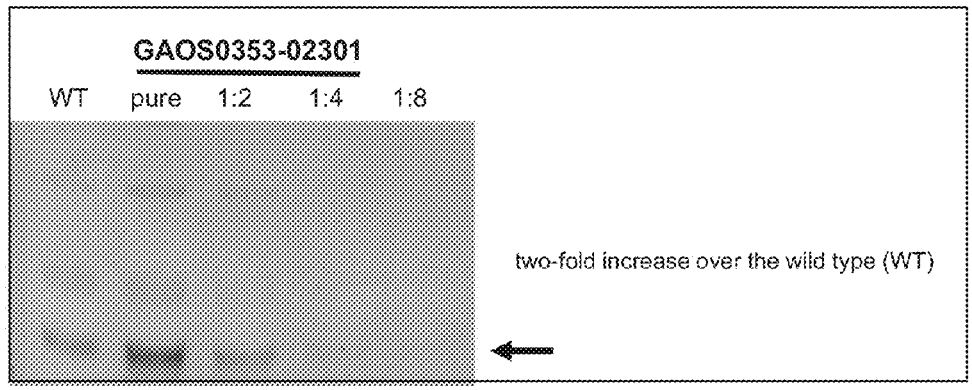
FIG. 1A-1C shows zymograms of three genetically modified rice lines: GAOS 0353-02301 (FIG. 1A), GAOS 0353-01301 (FIG. 1B), and GAOS 0353-01502 (FIG. 1C), for determining the SSII activity in comparison with the wild type.

The present invention relates to a process for increasing the phosphate content of starches of genetically modified plant cells to 150 to 500% in comparison with starches from corresponding genetically nonmodified wild-type plant cells (100%), wherein
a) a plant cell is genetically modified by the introduction of a foreign nucleic acid molecule coding for a soluble starch synthase II and
b) this soluble starch synthase II is overexpressed.

In the context of the present invention, the term "phosphate content of starch" is understood as meaning phosphate groups which are covalently bonded to the glucose monomers of the starch.

In the context of the present invention, the term "increase in the phosphate content of starches" is understood as meaning an increase of the phosphate content in the C6 position to 150-500%, preferably to 160-400% and especially preferably to 170-380% in comparison with starch from corresponding wild-type plant cells (100%).

In the context of the present invention, the term "phosphate content in position C6" is understood as meaning the content in phosphate groups which are bound at the carbon atom position "6" of the glucose monomers of the starch. In principle, the positions C3 and C6 of the glucose units can be phosphorylated in starch in vivo. In the context of the present invention, the phosphate content in position C6 (=C-6-P content) is determined via a glucose-6-phosphate determination by means of the visual enzyme assay described hereinbelow (Nielsen et al., 1994, Plant Physiol. 105, 111-117); (determination of the phosphate content at position C6 (C6-P content).

What was extremely surprising in the present invention was that it was possible to increase the phosphate content to markedly more than 150% in comparison with the wild type (100%).

In the context of the present invention, the elevation of the phosphate content of starches is effected in vivo, not in vitro, such as, for example, by chemical phosphorylation of a pre-extracted starch. Accordingly, the advantage of the present invention is that chemical agents used for the chemical phosphorylation can be dispensed with.

In the context of the present invention, the term "genetically modified plant cell" means that the plant cell is genetically modified, the genetic modification leading to an increased activity of a soluble starch synthase II (=SSII) in comparison with the SSII activity of a corresponding genetically nonmodified wild type plant cell.

In the context of the present invention, the term "wild-type plant cell" means that they are plant cells which act as starting material for the process according to the invention, i.e. whose genetic information, with the exception of the genetic modification which has been introduced and which leads to an increased activity of a soluble starch synthase II (=SSII), corresponds to that of a genetically modified plant cell.

In the context of the present invention, the term "corresponding" means, when comparing a plurality of objects, the objects in question, which are compared with one another, are maintained under identical conditions. In the context of the present invention, the term "corresponding" in the context of wild-type plant cells means that the plant cells which are compared with one another were grown under identical culture conditions and that they preferably have the same age (in culture).

The term "age in culture" is understood as meaning the period over which a (plant) organism spends/grows in a nutrient medium. This may be for example the period of time from sowing to harvesting, or else the period of time during which plant cells are cultured in a tissue culture medium up to a certain developmental stage. In the context of the present invention, this means that the plant cells which are compared with one another spend the same developmental period of time under the same culture conditions.

In the context of the present invention, the term "foreign nucleic acid molecule" is understood as meaning such a molecule which either does not occur naturally in the corresponding wild-type plant cells or which does not occur naturally in corresponding wild-type plant cells in the specific spatial arrangement or one which is localized at a location, in the genome of the plant cell, where it does not occur naturally. The foreign nucleic acid molecule/polynucleotide is preferably a recombinant molecule which consists of various elements whose combination or specific spatial arrangement does not occur naturally in plant cells. This can be verified for example with the aid of a Southern blot analysis.

Within the context of the present invention, the term "overexpressed" means an increase of the enzymatic activity of SSII proteins in the genetically modified plant cells in comparison to corresponding, genetically nonmodified wild-type plant cells. For the purposes of the present invention, the term "overexpressed" furthermore also means that plants or plant cells which naturally do not have any detectable SSII activity, will, after the genetic modification according to the invention, in which a foreign nucleic acid molecule coding for a soluble starch synthase II is introduced into the genome of a plant cell, have an SSII activity which can be detected by means of a zymogram. The increase of the enzymatic activity of SSII proteins in the cells is preferably determined with the aid of zymograms as described hereinbelow ("determination of the SSII activity by means of activity gel").

In this context, an increase of the SSII activity means an increase of the SSII activity in comparison with corresponding, non-genetically-modified cells, to at least 200%, in particular to 350-2000%, preferably to 600-1500% and especially preferably to 700-1200%. In the context of the present invention, an "increase of the SSII activity" also means that plants or plant cells which have no detectable SSII activity will, after the genetic modification according to the invention, in which a foreign nucleic acid molecule coding for a soluble starch synthase is introduced into the genome of a plant cell, have a detectable SSII activity.

In the context of the present invention, the term "soluble starch synthase II" is understood as meaning the class II of soluble starch synthase proteins (ADP-glucose 1,4-α-D-glucan 4-α-D-glucosyltransferase; EC 2.4.1.21). Soluble starch synthases catalyze a glycosylation reaction in which glucose residues of the substrate ADP-glucose are transferred to α-1,4-linked glucan chains with formation of an α-1,4-linkage (ADP-glucose+{(1,4)-α-D-glucosyl}(N) <=>ADP+{(1,4)-α-D-glucosyl}(N+1)).

The structure of SSII proteins shows a sequence of specific domains. At the "N" terminus, SSII proteins have a signal peptide for the transport into plastids. An N-terminal region and a catalytic domain follow in the direction of the C terminus (Li et al., 2000, Plant Physiology 123, 613-624). Further analyses based on primary sequence comparisons (http://hits.isb-sib.ch/cgi-bin/PFSCAN) of a variety of SSII proteins have revealed that SSII proteins have three specific domains. These domains comprise the amino acids which are encoded by the nucleotides: by 1190 to 1279 (=region 1), by 1493 to 1612 (region 2) and by 2147 to 2350 (region 3) of the sequence of the wheat SSII gene which is shown in Seq ID No. 1.

In the context of the present invention, an SSII protein is therefore understood as meaning a soluble starch synthase whose amino acid sequence has at least 86%, preferably at least 93% and especially preferably 100% identity with the region 1 shown in Seq ID No. 3 and at least 83%, preferably at least 86% and especially preferably 100% identity with the region 2 shown in Seq ID No. 4 and at least 70%, preferably at least 82%, by preference 86%, particularly preferably 98% and especially preferably 100% identity with the region 3 shown in Seq ID No. 5.

In the context of the present invention, the term "identity" is understood as meaning the percentage of amino acids which agree with amino acids of other proteins (identity). The identity is preferably determined with the aid of computer programs. If sequences which are compared with each other are different in length, the identity is to be determined in such a way that the number of amino acids which the shorter sequence shares with the longer sequence determines the percentage identity. The identity can be determined routinely by means of known computer programs which are publicly available such as, for example, ClustalW (Thompson et al., (1994) Nucleic Acids Research 22: 4673-4680).

ClustalW is made publicly available by Julie Thompson (Thompson@EMBL-Heidelberg.DE) and Toby Gibson (Gibson@EMBL-Heidelberg.DE), European Molecular Biology Laboratory, Meyerhofstrasse 1, D-69117 Heidelberg. ClustalW can likewise be downloaded from various internet pages, inter alia the IGBMC (Institut de Génétique et de Biologie Moléculaire et Cellulaire, B.P.163, 67404 Illkirch Cedex, France; ftp://ftp-igbmc.u-strasbg.fr/pub/) and the EBI (ftp://ftp.ebi.ac.uk/pub/software/), and all mirrored EBI internet pages (European Bioinformatics Institute, Wellcome Trust Genome Campus, Hinxton, Cambridge CB10 1SD, UK).

It is preferred to use the ClustallW computer program Version 1.8 to determine the identity between the proteins described herein and other proteins. The following parameters are to be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

It is preferred to use the ClustalW computer program Version 1.8 to determine the identity between the nucleotide sequences of the nucleic acid molecules described herein and the nucleotide sequence of other nucleic acid molecules. The following parameters are to be set: KTUPLE=2, TOPDIAGS=4, PAIRGAP=5, DNAMATRIX:IUB, GAPOPEN=10, GAPEXT=5, MAXDIV=40, TRANSITIONS: unweighted.

In the context of the present invention, the term "increasing the SSII activity" means increasing the SSII activity in comparison with corresponding, non-genetically-modified wild-type rice plants or wild-type rice plant cells by at least 100%, in particular by 200%-2000%, preferably by 400%-1400% and especially preferably by 500%-900%. In the context of the present invention, the SSII activity is detected using the method described hereinbelow ("determining the SSII activity by means of activity gel"). In the context of the present invention, "increasing the SSII activity" also means that plants or plant cells which have no detectable SSII activity will, after genetic modification according to the invention, where a foreign nucleic acid molecule coding for a soluble starch synthase is introduced into the genome of a plant cell, show a detectable SSII activity.

In a preferred embodiment, the process according to the invention is furthermore one wherein the foreign nucleic acid molecule takes the form of the coding region of a heterologous soluble starch synthase II.

In the context of the present invention, a "heterologous soluble starch synthase II" is understood as meaning a soluble starch synthase II which does not occur naturally in the plant cell but whose coding DNA sequence is introduced into the cell by means of recombinant methods, such as, for example, transformation of the cell. In this context, the coding DNA sequence originates from a plant species other than that of the transformed plant cell or plant, or is not under the control of its own promoter. The coding DNA sequence preferably originates from a plant genus other than that of the transformed plant cell or plant.

In the context of the present invention, the term "plant genus" is understood as meaning a hierarchical level of biological systematics. A genus comprises one or more than one species. An example of a genus is *Triticum* L. (wheat). All the species within a genus always have a binomial name which, besides the generic name, additionally contains a species epitheton. *Triticum aestivum* L. (common bread wheat) is, accordingly, a species of the genus *Triticum*.

In the context of the present invention, the term "SSII gene" is understood as meaning a nucleic acid molecule or polynucleotide (DNA, cDNA) which codes for a "soluble starch synthase II". In a further embodiment, the SSII gene originates from a monocotyledonous plant. In a preferred embodiment, the SSII gene originates from wheat.

In a further preferred embodiment, the process according to the invention is one wherein a soluble starch synthase II from a monocotyldenous plant is used. In an especially preferred embodiment, the SSII is coded by the coding region of the nucleotide sequence shown in SEQ ID No.1 or has the amino acid sequence shown in SEQ ID No. 2.

The genetically modified plants whose starch is modified by the process according to the invention can belong to any plant species, i.e. both to the monocotyledonous plants and to the dicotyledonous plants. The plants preferably take the form of agricultural crop plants, i.e. plants which are grown by man for the purposes of nutrition or for technical, in particular industrial, purposes, and their cells. The process according to the invention is preferably applied in starch-storing plants such as, for example, peas, potato, sweet potato, cassaya, maize and rice.

In an especially preferred embodiment, the process according to the invention is carried out on rice plants.

The present invention relates furthermore to a rice starch with a DSC T-onset temperature of between 70° C. and 80° C.

The thermal characteristics of the starch of the rice endosperm and of the rice flours can be analyzed by differential scanning calorimetry=DSC. These are shown as the gelatinization temperature with the values DSC T-onset (=lowest gelatinization temperature) and DSC T-peak (=highest gelatinization temperature).

In the context of the present invention, the term "DSC T-onset temperature" is therefore understood as meaning the temperature which represents the beginning of the phase transition of the starch or flour sample. It is characterized as the projection of the base line and the tangent drawn at the ascending flank of the peak across the flex point.

Surprisingly, the rice plants according to the invention synthesize starches with DSC T-onset temperatures of between 70° C. and 80° C., in particular between 77° C. and 80° C. The rice starch according to the invention in particular has a DSC T-onset of between 72 and 79° C., preferably between 74° C. and 79° C., very particularly preferably between 76° C. and 78° C.

In a further embodiment, the rice starches according to the invention have an elevated DSC T-peak temperature (DSC T-peak).

Surprisingly, the rice plants according to the invention synthesize starches with a DSC T-peak temperature of between 80° and 87° C., preferably between 81 and 86° C. A rice starch according to the invention with a DSC T-peak temperature of between 82° C. and 83° C. is especially preferred.

In the context of the present invention, the term "DSC T-peak temperature" is understood as meaning the temperature at which the DSC curve has reached a maximum and the first differentiation of the curve is zero.

In the context of the present invention, the "DSC T-onset" and the "DSC T-peak" temperatures are determined by the method described hereinbelow ("thermal analysis of rice flour/starch by means of differential scanning calorimetry").

The fact that the DSC T-onset temperature of the rice starch according to the invention was elevated to such a degree was extremely surprising for a person skilled in the art, in particular because the starch phosphate content of the rice starches according to the invention was simultaneously elevated. This is because it has been postulated to date that an increased degree of phosphorylation leads to destabilization of the double halices and the crystalline order in the starch granule, which should result in a reduced DSC T-onset temperature (Safford et al., (1998) Carbohydrate Polymers 35: 155-168). Native starches with a high degree of phosphorylation usually lose their crystallinity at markedly lower temperatures than comparable starches with a low phosphate content.

However, the use of granular rice starches is desirable in a large number of thermal processing steps and applications. What is therefore particularly advantageous is the surprisingly high DSC T-onset or T-peak temperature of the rice starches according to the invention, in other words the surprisingly high pasting temperature during the RV analysis of the rice flours according to the invention, since this property makes it possible to retain the structure of the starch granules at elevated process temperatures.

In a further embodiment, the rice starch according to the invention has a phosphate content in position C6 (C-6-P) of between 0.70 and 2.5 nmol phosphate per milligram of hydrolyzed starch.

In a preferred embodiment, the rice starch according to the invention has a phosphate content at position C6 between 0.9 and 2.3 nmol phosphate per milligram of starch. In an especially preferred embodiment, the phosphate content of position C6 is between 1.5 and 2.0 nmol phosphate per milligram of starch.

Furthermore, the present invention extends to derivatized rice starch comprising the rice starch according to the invention.

In the context of the present invention, the term "derivatized rice starch" means a rice starch according to the invention whose properties have been modified with the aid of, for example, thermal, chemical, enzymatic or mechanical processes after its isolation from plant cells.

The rice starches according to the invention are better suited as starting material for the preparation of derivatized rice starches than conventional starches since, as the result of the higher starch phosphate content, they contain a higher proportion of reactive functional groups, and since the rice starch according to the invention has a higher pasting temperature, or higher thermal stability, than starches with a comparable phosphate content.

The present invention therefore also relates to methods of producing a derivatized rice starch according to the invention, wherein the rice starch according to the invention is subsequently modified.

In particular, the derivatized rice starch according to the invention takes the form of starch treated thermally and/or with acid.

In a further embodiment, the derivatized rice starches take the form of starch ethers, in particular starch alkyl ethers, O-allyl ethers, hydroxylalkyl ethers, O-carboxylmethyl ethers, nitrogen-containing starch ethers, phosphate-containing starch ethers or sulfur-containing starch ethers.

In a further embodiment, the derivatized rice starches take the form of crosslinked starches.

In a further embodiment, the derivatized rice starches take the form of starch graft polymers.

In a further embodiment, the derivatized rice starches take the form of oxidized starches.

In a further embodiment, the derivatized rice starches take the form of starch esters, in particular starch esters which have been introduced into the starch by using organic acids. Especially preferably, they take the form of phosphate, nitrate, sulfate, xanthate, acetate or citrate starches.

The derivatized rice starches according to the invention are suitable for a variety of uses in the pharmaceutical industry, in the food sector and/or in the nonfood sector. Methods of preparing derivatized starches according to the invention are known to the skilled worker and extensively described in the general literature. An overview of the preparation of derivatized starches is found, for example, in Orthoefer (in Corn, Chemistry and Technology, 1987, eds. Watson and Ramstad, Chapter 16, 479-499). The derivatization of rice starches is also described for example in Shih and Daigle (2003, Nahrung 47(1): 64-67).

The present invention furthermore relates to the use of rice starches according to the invention for the preparation of derivatized starch.

The rice starch according to the invention, in native or derivatized form, is suitable for a variety of applications in the food or nonfood sector. A further embodiment comprises the use of the derivatized rice starch according to the invention in the industrial sector. As the result of the small granule size of the rice starch according to the invention, the latter is also particularly suitable for the manufacture of photographic paper.

The present invention furthermore extends to a composition comprising the rice starch according to the invention.

In a further embodiment, the present invention extends to rice flour which comprises the rice starch according to the invention.

In a further embodiment, the rice flours according to the invention have DSC T-onset temperatures of between 72° C. and 81° C., preferably between 74° C. and 80° C., in particular between 77° C. and 80° C. A rice flour according to the invention with a DSC T-onset temperature of between 76° C. and 79° C. is especially preferred.

In a further embodiment, the rice flours according to the invention have DSC T-peak temperatures of between 81° C. and 90° C., preferably between 82° C. and 86° C. A rice flour with a DSC T-peak temperature of between 82° C. and 85° C. is especially preferred.

In a further embodiment, the rice flours according to the invention have an RVA PT pasting temperature of between 75 and 90° C., preferably of between 78° C. and 88° C., in particular between 83° C. and 86° C. and especially preferably of between 80° C. and 85° C. in the RVA (Rapid Visco Analyser) analysis.

In the context of the present invention, the term "pasting temperature" (RVA PT) means that the value measured at the beginning of the viscosity development in accordance with RVA analyses is the temperature at which the viscosity curve during the heating process leaves the baseline and at which the viscosity changes by more than 36cP within a period of 0.1 minute.

In the context of the present invention, the "RVA PT pasting temperature" is determined with the aid of the method "analysis of rice flour by means of Rapid Visco Analyser (RVA)" which is described hereinbelow.

In comparison with rice flours from corresponding wild-type rice plants, the rice flour according to the invention has an elevated pasting temperature (RVA PT).

In the context of the present invention, the term "elevated pasting temperature (RVA PT)" means that the pasting temperature (RVA PT) is 5° C. to 15° C., in particular 6° C. to 14° C., preferably 8° C. to 12° C., higher in comparison with the pasting temperature RVA PT of rice flours from corresponding wild-type rice plants.

In a further embodiment, the rice flour according to the invention features a reduced period between reaching the pasting temperature and reaching the peak viscosity.

In the context of the present invention, the term "reduced period between reaching the pasting temperature and reaching the peak viscosity" (peak time–pasting time) means that the difference in terms of time in accordance with RVA analysis as described hereinbelow amounts to 40 seconds to 130 seconds, especially preferably 50-100 seconds and especially preferably 60-75 seconds.

In a further embodiment, the present invention relates to a method of preparing a rice flour according to the invention, wherein rice grains according to the invention, preferably polished rice grains according to the invention, are ground. Methods for polishing and grinding rice grains are known to the skilled worker and described, for example, in Fitzgerald et al. (2003, J. of Agrocult. And Food Chemistry 51: 2295-2299) or in Ramesh et al. (1999, Carbohydrate Polymers 38: 337-347).

A "rice grain" is taken by the skilled worker to mean the mature, fertilized flower of a rice plant.

The present invention also extends to the use of a rice flour according to the invention for the preparation of foodstuffs and/or animal feed.

The present invention furthermore relates to a composition which comprises the rice flour according to the invention.

In a further embodiment, the present invention extends to a rice grain which comprises the rice starch according to the invention.

In a preferred embodiment, it takes the form of a processed rice grain.

Processing is understood by the skilled worker to mean the conversion of crude (paddy) rice into brown or white rice; processing methods are known to the skilled worker and described, inter alia, in Fitzgerald et al. (2003, J. of Agrocult. and Food Chemistry 51: 2295-2299) or in Ramesh et al. (1999, Carbohydrate Polymers 38: 337-347).

In a further embodiment of the present invention, the rice grain according to the invention can be used for cooking.

In a further embodiment, the rice grain has altered characteristics after cooking.

In the context of the present invention, "altered characteristics after cooking" is understood as meaning that the characteristics of the rice grain which relate to quality, such as, for example, texture or the grain hardness and the stickiness of the grains after cooking, in particular after cooling or reheating of the cooked rice, are altered.

In a preferred embodiment, the rice grains according to the invention have a stickiness of −10 to −200 g, preferably −12 g to −150 g, especially preferably −15 g to −130 g (measured in g of tensile force).

The term "stickiness" is understood by the skilled worker as meaning the effect of water uptake and heating during cooking and the consistency of the rice grains and the adhesion of the rice grains to other rice grains or other surfaces (for example fork, chopsticks and the like) which this entails after cooking. In the context of the present invention, stickiness is to be understood as meaning the maximum negative force (tensile force) which is measured by means of texture analyzer after previously compressing the optimally cooked rice grains, as described in the method "determining the cooking characteristics and the texture of cooked rice grains". A high negative value in this context means a higher stickiness than a lower negative value. In the context of the present invention, "optimally cooked rice grains" are understood as meaning rice grains which are cooked for two more minutes after having reached the minimum cooking time (when 90% of the grains no longer have a white center, as determined in the glass sheet test as described by Juliano 1984; J. of Tex. Studies 15: 357-376).

In the present invention, the stickiness is measured on optimally cooked rice grains, rice grains which have been stored for 22 hours at 4° C. and then again brought to room temperature, or rice grains which, after storage at 4° C. (for 22 hours), have been reheated for 5 minutes at 80° C. in an oven or which have been reheated after storage at 4° C. (22 hours) with the aid of a microwave (600 W/3 min).

Reheating is understood by the skilled worker as meaning reheating once to four times the rice which has been cooked and, inbetween reheating, cooled, for example by allowing to stand at room temperature, using a microwave, an oven, a water bath or a hot cabinet; preferably, it is understood as meaning a single reheating path.

Since "stickiness" is an important quality parameter for rice, the rice grains according to the invention offer advantageous uses. This includes, above all, the field of application in semifinished products which are only cooked briefly when produced, then dried again and reheated or boiled up only shortly before their final consumption (for example on domestic premises, in canteens), without any adverse effect on flavor and consistency.

A further quality parameter in this context is the extension of the grain dimension upon boiling in water in the direction of the longitudinal axis. Such a change in shape is an important visual quality parameter, in particular in the case of long-grain rice.

In a further embodiment of the present invention, the rice grains according to the invention are distinguished by the fact that they have an elongation rate (ER) of from 1.50 to 1.90, especially preferably of from 1.55 to 1.80 and particularly preferably of from 1.60 to 1.70.

In a further embodiment of the present invention, the rice grains according to the invention have an increased elongation rate in comparison with rice grains of corresponding wild-type rice plants.

In the context of the present invention, an increased elongation rate is understood as meaning an elongation rate which is increased by 5% to 25%, preferably by 10% to 20%, especially preferably by 14% to 18%.

In the present context, the "elongation rate" is understood as meaning the ratio of the grain length of the cooked rice grain to the grain length of the uncooked rice grain. The grain length is measured in mm, as is described, for example, in the method "measuring the change in grain dimensions by cooking"; the measurement is preferably carried out using a slide gage.

In a further embodiment, the rice grains according to the invention have a CDC value of from 2.8 to 6.2, preferably of from 3.5 to 5.5 and especially preferably of from 4.0 to 5.0.

The "CDC value" (CDC=coefficient of dimensional changes) is understood as meaning the ratio of the dimensional change along the length to the dimensional change along the width as the result of cooking, i.e. the ratio of the grain length in the cooked state (Lc) to the uncooked state (Lu) in relation to the ratio of the grain width in the cooked state (Wc) to the uncooked state (Wu)=(Lc/Lu)/(Wc/Wu).

A further subject matter of the present invention relates to a composition comprising at least one rice grain according to the invention.

The present invention furthermore comprises a rice plant on which at least one rice grain according to the invention grows and/or comprising the rice starch according to the invention.

In a further embodiment, the present invention comprises genetically modified rice plant cells and rice plants wherein the genetic modification leads to an increased activity of the soluble starch synthase II (SSII) in comparison with corresponding genetically non-modified wild-type rice plants, or wild-type rice plant cells.

It was furthermore surprising that the rice starch according to the invention has a modified distribution of certain side chains in comparison with rice starch from corresponding wild-type plant cells or wild-type plants.

In a further embodiment of the present invention, it has emerged that the degree of amylopectin side chains with a dp (=degree of polymerization) of from 20 to 25 is increased by 5-35% in comparison with rice starch from corresponding wild-type rice plants.

In the context of the present invention, the term "increasing the content of amylopectin side chains with a dp (=degree of polymerization) of from 20 to 25" means increasing the content of amylopectin side chains with a DP of 20-25 by 5%-35%, preferably by 6%-30%, especially preferably by 8%-24%, in comparison with the content of side chains with a DP of 20-25 of amylopectin from corresponding wild-type rice plant cells or wild-type rice plants.

In a further embodiment of the invention, the content of amylopectin side chains with a dp of from 6 to 10 is reduced.

In the context of the present invention, the term "reducing the content of amylopectin side chains with a dp of from 6 to 10" means reducing the content of amylopectin side chains with a DP of 6-10 by 20%-60%, preferably by 25%-55%, especially preferably by 30%-55%, in comparison with a content of side chains with a DP of 6-10 of amylopectin from corresponding wild-type rice plant cells or wild-type rice plants.

In the context of the present invention, the determination of the side-chain distribution is carried out by means of the method described hereinbelow ("processing rice flour/starch for analyzing the amylopectin side chain distribution by means of high-pressure anion exchange chromatography"). The percentage of short side chains is determined via the determination of the percentage of a specific side chain of the total of all side chains. The total of all side chains is determined via the determination of the total area under the peaks which represent the degrees of polymerization from DP 6 to 48 in the HPLC chromatogram. The percentage of the specific side chain of the total of all side chains is determined via the determination of the ratio of the area under the peak which represents this side chain in the HPLC chromatogram relative to the total area. To determine the peak areas, the program Chromelion 6.60 from Dionex, USA, may be used for example.

In the context of the present invention, the term "wild-type rice plant" is taken to mean rice plants which act as starting material for the rice plants according to the invention, i.e. whose genetic information, apart from the genetic modification introduced which leads to an increase in the activity of a soluble starch synthase II (SSII), corresponds to that of a genetically modified rice plant.

Preferably, the term "wild-type rice plant" refers to the variety M202, a rice variety with S-type amylopectin with a value of 25.2%, grains of which have been deposited on Nov. 17, 2005, at the NCIMB Ltd. depository, Ferguson Building, Craibstone Estate, Bucksburn, Aberdeen, Scotland, AB21 9YA, United Kingdom as number NCIMB 41352.

In the context of the process according to the invention, the genetic modification preferably comprises the introduction of at least one foreign nucleic acid molecule coding for a soluble starch synthase II (SSII) into the genome of a plant cell, said introduction of at least one foreign nucleic acid molecule resulting in the fact that the starch obtainable from the genetically modified plant cell and the plant regenerated therefrom has, as the result of the expression of the SSII which has been introduced, an increased content of phosphate in the C6 position in comparison with corresponding genetically nonmodified wild-type plant cells.

In a further embodiment of the present invention, the introduction of at least one foreign nucleic acid molecule results in the synthesis of a rice starch according to the invention.

In a preferred embodiment, the rice plants and rice plant cells according to the invention are those wherein the foreign nucleic acid molecule is the coding region of a heterologous soluble starch synthase II.

A multiplicity of techniques is available for introducing DNA into a plant host cell. These techniques comprise transformation of plant cells with T-DNA using *Agrobacterium tumefaciens* or *Agrobacterium rhizogenes* as transformation agent, the fusion of protoplasts, the injection, the electroporation of DNA, the introduction of the DNA by means of the biolistic approach, and other possibilities.

The transformation of monocotyledonous plants by means of vectors based on transformation with *Agrobacterium* has been described for example in Chan et al., 1993, Plant Mol. Biol. 22: 491-506; Hiei et al., 1994, Plant J. 6: 271-282; Deng et al., 1990, Science in China 33: 28-34; Wilmink et al., 1992, Plant Cell Reports 11: 76-80; May et al., 1995, Bio/Technology 13: 486-492; Conner and Domisse, 1992, Int. J. Plant Sci. 153: 550-555 and in Ritchie et al, 1993, Transgenic Res. 2: 252-265. Alternative systems for the transformation of monocotyledonous plants are: the transformation by means of the biolistic approach (Wan and Lemaux, 1994, Plant Physiol. 104: 37-48; Vasil et al., 1993, Bio/Technology 11: 1553-1558; Ritala et al., 1994, Plant Mol. Biol. 24: 317-325; Spencer et al., 1990, Theor. Appl. Genet. 79: 625-631), the transformation of protoplasts, the electroporation of partially permeabilized cells, and the introduction of DNA by means of glass fibers. Successful transformation of various cereal species has for example been described for barley (Wan and Lemaux, supra; Ritala et al., supra; Krens et al., 1982, Nature 296: 72-74), for wheat (Nehra et al., 1994, Plant J. 5: 285-297), rice (Ishida et al., 1996, Nature Biotechnology 14 (6): 745-750) and maize (Koziel et al. (1993), Biotechnology 11: 194-200).

The regeneration of the genetically modified plant cells of the process according to the invention results in the generation of genetically modified plants whose genetic information corresponds to that of a corresponding genetically nonmodified wild-type plant and which contains the same introduced genetic modification for increasing the activity of a soluble starch synthase II which is already present in the genetically modified plant cells of the process according to the invention.

In a preferred embodiment, the present invention relates to rice plants from the *japonica* group (*Oryza sativa* var. *japonica*), which comprises short-grain and medium-grain rice varieties such as, for example, glutinous rice, pudding rice, mochi rice, nishiki rice, ribe rice, red rice, black rice, sushi rice. In an especially preferred embodiment of the present invention, rice wild-type plants from the *japonica* group are used as starting material for generating the rice plants according to the invention.

In a further, very especially preferred embodiment, the present invention relates to rice plants with S-type amylopectin.

In rice amylopectin, L- and S-types may be distinguished. L-type amylopectin is predominantly found in rice from the *indica* group, while S-type amylopectin, in contrast, is found predominantly in rice from the *japonica* group. In the context of the present invention, S-type amylopectin is distinguished by the fact that, in comparison with the L-type, the amount of the short alpha-1,4-glucan chains (DP<=10) amounts to more than 20% of the total of the α-1,4-glucan chains of DP<=24 (Nakamura 2002, Starch 54: 117-131).

In a very especially preferred embodiment, the present invention comprises genetically modified rice plants (*Oryza sativa* var. *japonica*) of the transformants GAOS0353-02301, GAOS0353-01301 and GAOS0353-01502. Seed of the transformant M202 GAOS0353-01502 was deposited on 17.11.2005 at the NCIMB Ltd., Ferguson Building, Craibstone Estate, Bucksburn, Aberdeen, Scotland, AB21 9YA, United Kingdom, under the number NCIMB 41353.

In a further embodiment, the rice flour according to the invention has a lower content of apparent amylose than rice flour from corresponding wild-type rice plants. In the context of the present invention, the apparent amylose content is preferably determined with the aid of the method "determination of the apparent amylose content" described hereinbelow. In a preferred embodiment, the apparent amylose content of the rice flour according to the invention is reduced by 10% to 20%, especially preferably by 12% to 18% and very especially preferably by 13% to 15% in comparison with the apparent amylose content in flour from corresponding wild-type rice plants.

In a further embodiment of the invention, the foreign nucleic acid molecule introduced, which codes for a soluble starch synthase II, is under the control of an endosperm-specific promoter. Endosperm-specific promoters make it possible specifically to increase the amount of transcript of the foreign nucleic acid molecules coding for a soluble starch synthase II in the endosperm of the plants according to the invention in comparison with the endosperm of corresponding wild-type plants.

It is preferred to use promoters for an endosperm-specific expression, such as, for example, the glutelin promoter from rice (Leisy et al. (1990) Plant Mol. Biol. 14: 41-50; Zheng et al. (1993) Plant J. 4:357-366), the HMWG promoter from wheat (Anderson et al. (1989) Nucleic Acid Res 17:461-462), GBSSII promoters from wheat (WO 02/02785), the USP promoter (Baumlein et al. (1991) Mol. Gen. Genetics 225: 121-128), the phaseolin promoter from bean (Kawagoe and Murai (1992) Plant J 2 (6):927-36), promoters of Zein genes from maize (Pedersen et al., (1982) Cell 29: 1015-1026; Quatroccio et al., (1990) Plant Mol. Biol. 15: 81-93), the shrunken-1 promoter (sh-1) from maize (Werr et al. (1985) EMBO J. 4:1373-1380) or the prolamin promoters from rice (Qu & Takaiwa (2004) Plant Biotechnology Journal, 2:113-125).

It is especially preferred to use the globulin promoter from rice (Nakase et al. (1996) Gene 170(2): 223-226).

In a further embodiment, the present invention relates to a method of generating a rice plant according to the invention, wherein a rice plant according to the invention is regenerated from a rice plant cell according to the invention, and wherein, after regeneration, those rice plants in which the overexpression of the soluble starch synthase II results in an increased SSII activity are selected.

In the context of the present invention, the term selection means that, within a population, a deliberately chosen trait is the criterion according to which plants which display this trait are grown on, while those which do not show the desired trait are discarded.

In the context of the present invention, plants which were selected were those which have the trait increased SSII activity.

The present invention furthermore relates to the propagation material of the genetically modified rice plants according to the invention, which contain the rice plant cells according to the invention.

In this context, the term "propagation material" comprises those parts of the plant which are suitable for the generation of progeny via the vegetative or sexual route. Those which are suitable for vegetative propagation are, for example, cuttings or callus cultures. Propagation material comprises for example fruits, seeds, seedlings, protoplasts, cell cultures and the like. The propagation material is preferably endosperm-containing grains.

Rice grains of rice plants according to the invention, comprising genetically modified plant cells, are a further subject matter of the present invention.

In a further embodiment, the present invention comprises a method of producing a modified rice starch according to the invention, comprising the extraction of the starch from a rice plant according to the invention and/or from rice grains according to the invention and/or from rice flour according to the invention. Extraction methods are known to the skilled worker and described for example in Wang and Wang (2004, Journal of Cereal. Science 39: 291-296) or Patindol and Wang (2003, J. Agric Food Chem. 51: 2777-2784).

In a further embodiment, the present invention relates to resistant starches whose digestibility is reduced by comparison with the digestibility of starches from wild-type plants.

The digestibility of foods is determined inter alia by the type of starch they contain. Many food constituents are degraded even on their way to, as well as inside, the stomach, and small bowel. Some starches are, however, degraded only in the large bowel and are therefore referred to as resistant starches (=RS). These can be divided into four types. The first type (RS 1) includes starch enclosed in intact cells. Its accessibility for digestive enzymes is therefore only poor. This applies for example to starch in whole or coarsely ground cereals grains and to part of the starch in legumes. The second type (RS 2) includes starch which is not digested in the native form in the small bowel. The reason in this case is the structure of the starch grains and the arrangement of the starch molecules in the starch grain. Included therein is for example the starch in raw potatoes, green bananas or amylose-rich corn varieties (amylomaize). The third type (RS 3) encompasses the so-called retrograded starch. This is produced after cooling of heated, starch-containing foodstuffs such as bread and cooked potatoes. During this, some of the starch molecules rearrange, and crystalline zones are formed and are inaccessible for digestive enzymes (e.g. amyloses). The fourth type (RS 4) includes indigestible chemically modified starch which is produced for example by crosslinking or esterification (acetylation, etc.).

The health-promoting effect of resistant starches consists in particular of their fermentation influencing bacterial reactions, increasing the stool weight and leading to the production of short-chain fatty acids which represent the main energy supplier for the cells of the large bowel mucosa. In addition, an important role in tumor inhibition is ascribed to butyrate (further details are to be found inter alia in Wisker (2001), UGB-Forum 01:75-77).

Glucose and/or insulin levels for example in consumers of bread containing a high proportion of whole cereals grains (and thus RS1) are lower than with bread made from finely ground cereals. A smaller rise in blood glucose has likewise been found with many legumes. This indicates that type 1 resistant starch influences the effect a foodstuff has on blood glucose. Besides blood glucose and insulin, also very important for burning off fats are carbohydrates. A continually fluctuating insulin level interferes with the burning of fats and additionally leads to an increased feeling of hunger. For this reason, carbohydrates whose digestibility is low or diminished and which thus lead to an only slight rise in the insulin level are advantageous. It is thus possible for such starches, in appropriate products, to meet all the requirements of a diet involving absorption of small amounts of carbohydrates (="Low Carb").

It has emerged that the starches of the method according to the invention exhibit a distinctly reduced digestibility by comparison with wild-type starch. This was apparent when the isolated starch (FIG. 3) was investigated. Thus, starches produced by the method according to the invention display a high nutritional quality which makes use possible both for an increased fiber diet and in the "Low Carb" area and beyond.

The person skilled in the art distinguishes the starches according to the time needed for digestion: starch which takes 20 minutes to be digested is named "rapid digested starch (RDS)", starch which takes 60 minutes is named "slow digestible starch (SDS)" and starch which is left over after 120 minutes is named "resistant starch (RS)".

Surprisingly, the digestibility of isolated starch is reduced. Starches with a 10 to 65% reduction in digestibility compared to the wild type are preferred, a reduction in digestibility of 10 to 55% is particularly preferred, a reduction of 12 to 45% is very particularly preferred and a 15 to 30% reduction is most particularly preferred.

This means, that the percentage of resistant starch RS in the starches according to the invention is increased in comparison with the wild type starch. The RS content is determined as the difference from total starch dry weight (100%) minus the percentage of deliberated glucose from total starch after 120 minutes (as described in method 15 below). In this context, an increase means an increase of the RS content to 100-750%, preferably to 150-700% and especially preferably to 200-600%.

In another embodiment, the rice starches according to the invention show an RS content of 15%-45%, preferably at 17%-40% and most preferred of 20%-38%.

The present invention further encompasses plants and plant cells which comprise a starch which has been produced by the method according to the invention and which exhibit a reduced digestibility by comparison with starch from corresponding wild-type plants, or wild-type plants.

Materials and Methods

The methods which follow were used in the examples. These methods can be used for carrying out the methods according to the invention; they represent specific embodiments of the present invention, but do not limit the present invention to these methods. The skilled worker knows that the invention can be carried out equally by modifying the described methods and/or by replacing individual methodological sections by alternative methodological sections. An exception is only the method "determination of the content of starch-bound glucose-6-phosphate", which, in the context of the present invention, is only to be carried out in the manner described hereinbelow under 14).

1) Plant Material and Cultivation

Rice plants: *Oryza sativa*, *japonica* group, variety M202.

Seed was deposited at the NCIMB Ltd. (National Collection of Industrial Bacteria, Ferguson Building, Craibstone Estate, Bucksburn; Aberdeen, AB21 9YA, UK) on 17.11.2005. Seed variety M202-wild type was given the deposit number NCIMB 41352; seed of the transformant M202-GAOS0353-01502 was given the deposit number NCIMB 41353.

The rice plants were grown in the greenhouse under the following regime conditions: Sowing: substrate: mixture of 100% sphagnum peat and 100 l sand/qm and clay: 180 kg/qm in 1.61 rose pots (manufacturer: H. Meyer, Germany). pH: 5.4-6.2; Grain manure: Hakaphos (Compo, Germany) 14% N-16% P-18% K+2% Mg; 2 kg/qm; Feeding: 3.5 g/plant up to flowering: $NH_4NO_3$ (1.75 g) and Flory 2 Basis (manufacturer: Euflor, Germany): 1.75 g; 3% N-16% P-15% K+5% Mg.

Temperature: day 28° C./night: 24° C. (16 h/8 h); relative atmospheric humidity: 85-95%; Light: 16 h, 350 µEinstein/s×qm 2) Origin of the Sequences and Constructs Used for the Transformation The sequence Ta_SSIIa from wheat was used for the transformation of rice. Isolation and cloning were carried out as described in WO 97-45545 (under the then name "pTaSS1"). The transformation vector used, AH32-191, is described in Example 1.

3) Transformation and Regeneration of Rice Plants Rice plants were transformed and regenerated by the method described by Ishida et al. (1996, Nature BioTechnology, 14 (6): 745-750).

4) Processing of Rice Grains

To generate sufficient amounts of study materials, rice plants were grown under greenhouse conditions and harvested when fully mature. For further drying, the mature (i.e. fully developed) rice grains were stored for 3-7 days at 37° C.

Thereafter, the grains are freed from the husks by means of a sheller (Laboratory Paddy sheller, Grainman, Miami, Fla., USA), and the resulting brown rice is processed by polishing for 1 minute (Pearlest Rice Polisher, Kett, VIIIa Park, Calif.) to give white rice. The latter is used as starting material for analyses of the whole grain such as, for example, alkali spreading value, grain dimensions, grain weight and the like.

To study the grain composition and the starch and flour characteristics, the white grains are milled by means of a laboratory mill (Cyclotec, Sample mill, Foss, Denmark) to give rice flour. The principle of the laboratory mill is that the mill stock leaves the milling chamber only when a particle size of less than 0.5 mm has been reached. The milling process is complete when all of the sample material has left the milling chamber.

5) Analysis of the Expression Level of Starch Synthase II by Means of Northern Blot The expression of the starch synthase II from wheat in rice was analyzed by means of Northern blot. To this end, three immature rice grains (approximately 15 days after flowering) were studied for each independent transgenic event. By way of homogenization, the frozen rice grains were shaken in a Retsch mill (model MM300) in a 96-well-plate with a 4.5 mm steel ball for 30 seconds at the frequency of 30 hertz. Thereafter, the RNA was isolated by means of Promega RNA extraction kit on the 96-well scale following the manufacturer's instructions (SV 96 Total RNA Isolation System, Order No. Z3505, Promega, Mannheim).

2 µg of RNA per sample were brought to a uniform volume and treated with an identical volume of RNA sample buffer (65% (v/v) formamide, 8% formaldehyde, 13% (v/v) gel buffer (see above), 50 µg/ml ethidium bromide). After heating (10 min, 65° C.) and immediate cooling on ice, the RNA was separated for approximately 2 hours at a constant amperage of 50-80 mA on a 1.2% strength (w/v) agarose gel (20 mM MOPS pH 8.0, 5 mM Na acetate, 1 mM EDTA, 6% (v/v) formaldehyde), using RNA running buffer (20 mM MOPS pH 8.0, 5 mM Na acetate, 1 mM EDTA).

Thereafter, the RNA was transferred to Hybond N membrane by means of a diffusion blot using 10×SSC (1.5 M NaCl, 150 mM Na citrate pH 7.0) and immobilized on the membrane by means of UV irradiation.

An approximately 1 kb SpeI/BspHI fragment of the plasmid AH32-191 (Bp 4568-5686), which constitutes the 5' region of the SSII cDNA, was used for hybridizing the Northern blot. The DNA fragment was radiolabeled by means of the Random primed DNA labeling kit from Roche (Order No. 1004 760) using $^{32}$P-α-dCTP in accordance with the manufacturer's instructions.

The Northern blot was preincubated for 4 hours at 60° C. with gentle shaking in a water bath with hybridization buffer (250 mM Na phosphate buffer pH 7.2, 1 mM EDTA, 6% (w/v) SDS, 1% (w/v) BSA) before the radiolabeled DNA was added for the hybridization. After incubation for 16 hours, the hybridization solution was removed, and the membrane was washed in the water bath in succession with 3×SSC and 2×SSC (see above) at 60° C. with gentle shaking to remove unspecifically bound DNA molecules. To detect labeled RNA, the membrane was autoradiographed on an x-ray film for one to three days at −70° C.

6) Determination of the SSII Activity by Means of Activity Gel

The different starch synthase activities in immature rice grains were detected by means of activity gels (zymograms), in which protein extracts are separated in a polyacrylamide gel under native conditions and subsequently incubated with suitable substrates. The reaction product formed (starch) was stained by means of Lugol's solution (2% (w/v) KI; 0.2% (w/v) $I_2$) in the gel.

Single immature rice grains (approximately 15 days post-flowering, measured from the day of beginning anthesis) were shock-frozen in liquid nitrogen and homogenized in 150-200 µl of cold extraction buffer (50 mM Tris/HCl pH 7.6, 2.5 mM EDTA, 2 mM DTT, 4 mM PMSF, 0.1% (w/v) glycogen, 10% (v/v) glycerol). After centrifugation (15 min, 13 000 g, 4° C.), the clear supernatent was transferred into a fresh reaction vessel and an aliquot of the extract was used for determining the protein content by the method of Bradford (1976, Anal Biochem 72: 248-254).

The protein extracts were separated by means of a continuous 7.5% strength polyacrylamide gel (7.5% AA/BAA 37.5:1; 25 mM Tris/HCl pH 7.6, 192 mM glycine, 0.1% (w/v) APS, 0.05% (v/v) TEMED) using single-concentrated running buffer (25 mM Tris/HCl, 192 mM glycine). Prior to loading the gel, a pre-run for removing free radicals was carried out for 30 minutes at 8 mA and 4° C. 15 µg of protein were applied for each sample and electrophoresed for 2-2.5 hours at 4° C.

Thereafter, the gels were incubated overnight at room temperature in 15 ml of incubation buffer (0.5M of sodium citrate pH 7.0, 25 mM potassium acetate, 2 mM EDTA, 2 mM DTT, 0.1% (w/v) amylopectin, 50 mM tricine/NaOH pH 8.5, 1 mM ADP-glucose), with continuous shaking. The starch formed was stained by means of Lugol's solution.

To determine the extent of the increase of the SSII activity by means of zymograms, protein extracts of the genetically modified lines were diluted stepwise and used in accordance with the above-described method. After staining the zymograms with Lugol's solution, the extent of the increase in activity was determined by visually comparing the intensity of the SSII band for the different dilutions with the undiluted wild type.

7) Extraction of Rice Starch from Rice Flour

The extraction of rice starch from rice flour was carried out by a method similar to that described by Wang and Wang (2004; Journal of Cereal Science 39: 291-296).

10 g of rice flour were incubated with 40 ml 0.05% (w/v) NaOH for 16-18 hours on a shaker at room temperature. Thereafter, the suspension was transferred into a Warring blender to complete the digestion and mixed for 15 seconds at low speed and then for 45 seconds at high speed. To remove coarser constituents (for example cell wall), the suspension was passed through a sieve of mesh size 125 µm and then a sieve of mesh size 63 µm. After centrifugation at 1500 rpm for 15 minutes (Microfuge 3.OR; Heraeus), the supernatent was decanted off, and the protein layer, which was at the surface of the pellet, was removed using a spatula. The remainder of the pellet was resuspended in 0.05% (w/v) NaOH, and the procedure described above was repeated.

Thereafter, the pellet was resuspended in water, and the pH of the suspension was brought to 6.5-7 using HCl. The rice starch obtained was washed with water (3 times in total), each wash step comprising sedimentation (1500 rpm, 15 min, RT), discarding the supernatent and resuspension in fresh water. Before the last wash step, the pH was again checked and, if appropriate, brought to pH 7 with HCl. The rice starch pellet of the last wash step was resuspended in acetone and sedimented, and the supernatent was discarded. After the pellet had again been resuspended in acetone, the suspension was poured into a petri dish and dried at room temperature in a fume cabinet for at least 18 hours.

In a last step, the rice starch was comminuted in a pestle and mortar to give a fine powder, which was employed directly in all further analyses.

8) Processing Rice Flour/Starch for Studying the Amylopectin Side-Chain Distribution by Means of High-Pressure Anion Exchange Chromatography For each sample, 10 mg of rice flour or rice starch were weighed into a 2 ml Eppendorf cup and treated with 250 µl 90% (v/v) of DMSO. After the sample had been dissolved with shaking at 60° C., 375 µl of water were added, and the mixture was incubated for one hour at 95° C. 300 µl of 16.7 mM sodium acetate, pH 3.5 and 0.5 U isoamylase from *Pseudomonas* sp. (Megazyme; Bray, Ireland) were added to 200 µl of the reaction mixture. After incubation for 24 hours at 37° C., a further 0.5 U isoamylase was added, and the incubation was continued for a further 24 hours.

For the chromatography, 100 µl of the reaction mixture were diluted 1:5 with water and subsequently filtered through Ultrafree-MC filtertubes (Millipore). Approximately 90 µl of the filtrate were injected.

```
Chromatography:
Method:
HPLC system:           GP 50 Dionex Gradient Pump
                       ED 50      Dionex Electrochem. Detector/PAD
                       AS 50      Autosampler
                       Column oven
Column:                Dionex CarboPac PA 100 4 x 250 mm (P/N 046110)
                       with guard column PA 100 4 x 50 mm (P/N 046115)
Equipment configuration:
```

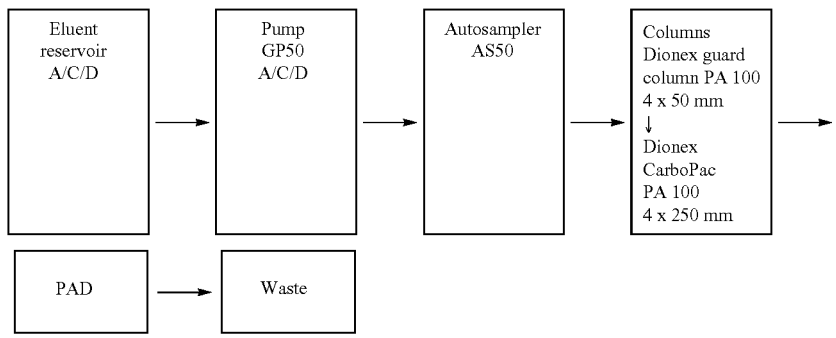

```
HPAEC Program:
    Pressure.LowerLimit =    50
    Pressure.UpperLimit =    3500
    %A.Equate = "NaOH 0.15M"
    %B.Equate = "NaOAc 1.0M"
    %C.Equate =    "NaOAc 1.0M in NaOH 0.15M"
    %D.Equate =    "Millipore Water"
    ECD.Data_Collection_Rate =   1.0
    Waveform Time = 0.00, Potential = 0.05
    Waveform Time = 0.20, Potential = 0.05, Integration = Begin
    Waveform Time = 0.40, Potential = 0.05, Integration = End
    Waveform Time = 0.41, Potential = 0.75
    Waveform Time = 0.60, Potential = 0.75
    Waveform Time = 0.61, Potential = -0.15
```

-continued

```
      Waveform Time = 1.00, Potential = −0.15
      Cell = On
      Flush Volume = 500
      Wait   FlushState
      NeedleHeight =   2
      CutSegmentVolume =   10
      SyringeSpeed =   4            ;
      Cycle =   0
      Wait For Temperature =   False
      Wait   SampleReady
0.000 Flow =       1.00
      %B = 0.0
      %C = 0.0
      %D = 0.0
      Curve =      5
      Load
      Inject
      Wait
      ECD.Autozero
      ECD_1.AcqOn
      Flow =       1.00
      %B = 0.0
      %C = 0.0
      %D = 0.0
      Curve =      5
5.000 Flow =       1.00
      %B = 11.0
      %C = 0.0
      %D = 0.0
      Curve =      5
      Flow =       1.00
      %B = 11.0
      %C = 0.0
      %D = 0.0
      Curve =      4
130.000 Flow =       1.00
      %B = 35.0
      %C = 0.0
      %D = 0.0
      Curve =      4
132.000   Flow =       1.00
      %B = 0.0
      %C = 100.0
      %D = 0.0
      Curve =      5
133.000   Flow =       1.00
      %B = 0.0
      %C = 100.0
      %D = 0.0
      Curve =      5
142.000   Flow =       1.00
      %B = 0.0
      %C = 0.0
      %D = 0.0
      Curve =      5
143.000   Flow =       1.00
      %B = 0.0
      %C = 0.0
      %D = 95.0
      Curve =      5
152.000   Flow =       1.00
      %B = 0.0
      %C = 0.0
      %D = 95.0
      Curve =      5
ECD_1.AcqOff
      End
```

Data evaluation is effected using Dionex Chromeleon v6.60 (Dionex Corporation, Sunnyvale, Calif., USA). The "Tutorial and User Manual" Version 6.60, March 2004, can be obtained from Dionex or downloaded from the Dionex home page (http://www.dionex.com).

To compare the chromatograms against one another, the peaks identified, of the different maltooligosaccharides, were mean-normalized for each chromatogram (sum of all peak areas=1). The evaluation was based on the "force common baseline", as described in Dionex Chromeleon v.6.60 for "log baseline". To do so, the log baseline is placed shortly before the first side-chain peak and up to the last evaluable peak of the shortest chromatogram of a measurement path; this forms the basis for calculating the last evaluable peak for all chromatograms.

9) Determination of the Cooking Characteristics and of the Texture of Cooked Rice Grains White rice grains which had been processed as described under 4) "Processing of rice grains" were used for determining the cooking characteristics. Prior to cooking, the grain dimensions and the grain weight were determined. Cooking entailed a water-rice ratio of 20:1.

The water was brought to the boil, the rice was added, and the heat input was reduced so that the water was simmering gently (during this process, the rice was stirred every 3 minutes). The minimum cooking time was determined by means of the glass sheet test as described by Juliano (1984; J. of Tex. Studies 15: 357-376). To do so, in each case 10 grains were squashed between two glass sheets at 1-minute intervals. The minimum cooking time was reached at the point in time at which 90% of the grains no longer showed a white center. The optimal cooking time was reached by prolonging the cooking process by two more minutes. The rice was strained through a sieve and cooled at room temperature. Thereafter, grain dimensions and weight of the cooked grains were again determined. The texture was measured using freshly cooked rice grains (approximately 1 h after cooking), on rice grains which had been stored for 22 hours at 4° C. and reheated to room temperature, and on rice grains which had been stored at 4° C. (for 22 hours) and then reheated using an oven or microwave. To reheat the cooked rice grains in the oven, the former were placed into an aluminum dish which was sealed with aluminum foil to avoid moisture losses. The dish was incubated in the oven for 20 minutes at 80° C. Reheating the grains in the microwave was carried out in a suitable microwave container for 3 minutes at 360 watt. After the two reheating processes, the grains were stored for 30 minutes at room temperature to ensure uniform temperature of the grains during the measurement.

Figure 2:
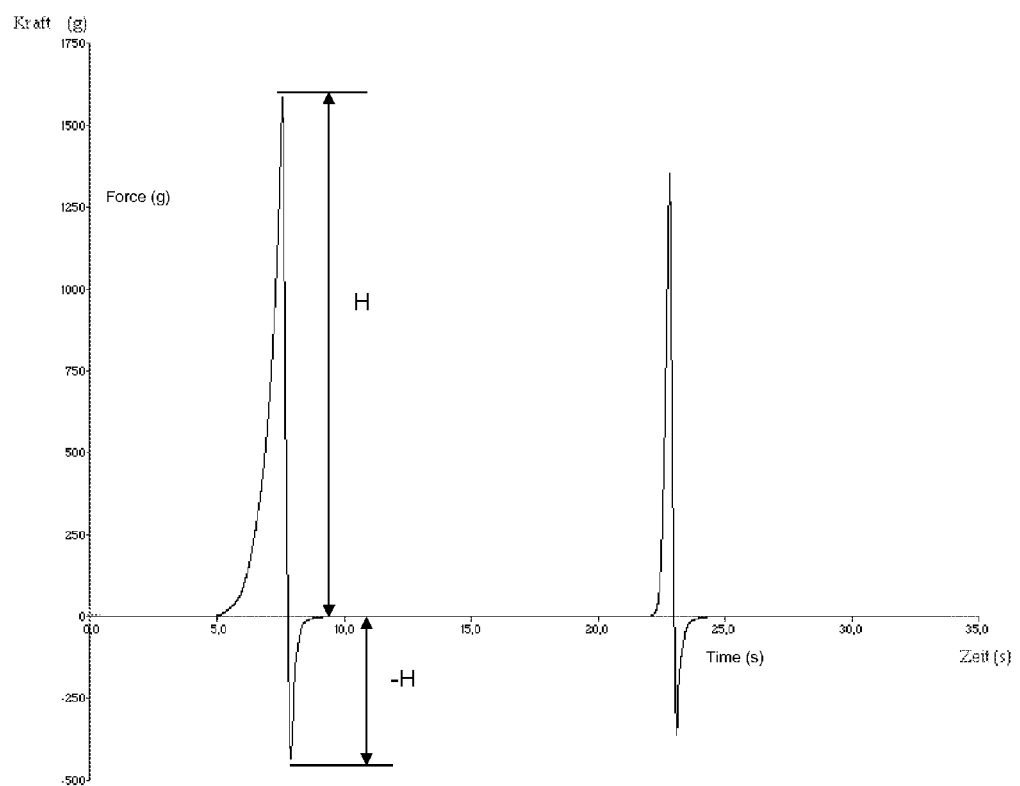
FIG. 2 depicts the determination of the texture of rice grains by showing hardness (H) of the cooked rice grains (maximum force during the first compression step) and stickiness (−H) (minimal force after the first compression step).

The texture of cooked rice from the above-described experiments was measured using a Texture Analyser TAXT2 (Stable Micro Systems, Godalming, UK) with a circular probe of diameter 2.5 cm and a double compression test as the measuring method (adapted from Champagne et al. (1998) Cereal Chem. 75 (2): 181-186). To do so, the rice grains were compressed in a first cycle, then decompressed and recompressed, the force which the grains apply to the probe (pressure or pull) being recorded continuously. Each sample to be analyzed was subjected to ten measurements on in each case three grains, the rice grains being placed under the probe in such a way that they neither touch one another nor extend beyond the edge of the probe. The parameters recorded were the hardness (H) of the cooked rice grains (maximum force during the first compression step) and the stickiness (—H) (minimal force after the first compression step), see FIG. 2. All measurements of one sample were evaluated separately, and means for the parameters in question were established thereafter.

10) Measuring the Change in Grain Dimension as the Result of Cooking

The grain dimensions (length, width and area) were determined using the software "SigmaScan Pro" Version 5.0.0 from Systat (Erkrath, Germany). To do so, in each case 30 rice grains (uncooked and cooked) were scanned, and the image formed was evaluated by means of the software. The following parameters were recorded or calculated:

$L_u$ - Grain length of uncooked rice
$L_c$ - Grain length of uncooked rice
$W_u$ - grain width of uncooked rice
$W_c$ - grain width of uncooked rice L/W ratio = $L_u/W_u$ or $L_c/W_c$
ER - elongation rate = $L_c/L_u$
CDC - Coefficient of dimensional change = $(L_c-L_u)/(W_c-W_u)$ 11) Thermal Analysis of Rice Flour/Starch by Means of Differential Scanning Calorimetry (=DSC)

Approximately 10 mg (dry weight) of rice flour or rice starch were weighed into stainless-steel pans (Perkin Elmer, "Large Volume Stainless Steel Pans" [03190218], Volume 60 µl) in an excess of double-distilled water (preferably 30 µl) and the pans were hermetically sealed. The sample was heated in a DSC apparatus, type Diamond (Perkin Elmer), from 20° C. to 150° C. at a heating rate of 10° C./minute. An empty sealed stainless-steel pan was used as reference. The system was calibrated using defined amounts of indium.

Data were analyzed by means of a software program from Pyris (Perkin Elmer, Version 7.0). Evaluable raw data were processed by analyzing the individual peaks of the first-order phase transitions to T-onset (° C.), T-peak (° C.), T-end (° C.) and dH (J/g) (the standard being the straight baseline).

DSC T-onset is characterized as the projection of the baseline and the tangent drawn at the ascending flank of the peak across the flex point. It characterizes the beginning of the phase transition.

The maximum temperature DSC T-peak refers to the maximum temperature at which the DSC curve has reached a maximum (i.e. the temperature at which the first differentiation of the curve is zero).

For the function used in Pyris (calc-peak area), a start temperature and a final temperature are input manually for the baseline fit.

12) Determination of the Apparent Amylose Content

The apparent amylose content was determined by a method adapted from Juliano (1971, Cereal Science Today 16 (10): 334-340).

For each sample, 50 mg of rice flour were weighed into 100 ml Erlenmeyer flasks (twice) and moistened in succession with 1 ml of 95% strength ethanol and 9 ml of 1 M NaOH.

In parallel, flasks with defined amounts of pure amylose are treated identically to the flour samples in order to establish a standard curve. The flasks were swelled briefly to mix the sample and subsequently incubated for 20 minutes in a boiling waterbath with gentle shaking. After cooling at RT for 5-10 minutes, the volume was made up to 100 ml with water.

100 µl aliquot was treated with 1 ml of test solution (10 mM acetic acid, 0.004% (w/v) $I_2$; 0.04% (w/v) KI), mixed thoroughly, and the absorption was determined at 620 nm against a corresponding blank value. The amylose content was calculated with the aid of the amylose standards which are used for establishing a calibration curve.

13) Analysis of Rice Flour by Means of Rapid Visco Analyser (RVA)

The principle of this analysis is based on subjecting a suspension of water and rice flour to a defined temperature and shearing protocol, during which the viscosity of the suspension is recorded continuously. The measuring instrument used is an RVA Super3 from Newport Scientific (Macclesfield, UK) with the corresponding software "Thermocline for Windows", Version 2.3.

For the analysis, 3 g of rice flour (weighed in as pure dry weight of the sample material, corrected for 0% moisture) were weighed into an analytical holder, treated with 25 ml of water, and the analytical holder was introduced into the apparatus after the latter had been provided with a stirrer.

The following temperature and shearing profile was applied:

| Time | Type | Value |
|---|---|---|
| 00:00:00 | Temp | 50° C. |
| 00:00:00 | Speed | 960 rpm |
| 00:00:10 | Speed | 160 rpm |
| 00:01:00 | Temp | 50° C. |
| 00:04:48 | Temp | 95° C. |
| 00:07:18 | Temp | 95° C. |
| 00:11:06 | Temp | 50° C. |
| 00:12:30 | End of test | |

After the measurement had ended, the following parameters were determined:
Peak viscosity (highest viscosity during measuring period 2 to 7 minutes)
Trough viscosity (lowest viscosity during measuring period 7 to 12 minutes)
Final viscosity (viscosity at the end of the measurement)
Breakdown=Peak−Trough
Setback=Final−Trough
Pasting temperature (temperature at which the viscosity changes by more than 36 cp during a time interval of 0.1 minute)
Peak time (time at which the peak viscosity is reached).

14) Determination of the Phosphate Content in the C6 Position (C6-P Content)

In starch, positions C3 and C6 of the glucose units may be phosphorylated. To determine the C6-P content of starch (modified method of Nielsen et al., 1994, Plant Physiol. 105: 111-117), 50 g of rice flour were hydrolyzed for 4 hours at 95° C. in 500 µl of 0.7 M HCl, with continuous shaking. Thereafter, the samples were centrifuged for 10 minutes at 15 500 g, and turbidities were removed from the supernatents by means of a filter membrane (0.45 µM). 20 µl of the clear hydrolysate were mixed with 180 µl of imidazole buffer (300 mM imidazole, pH 7.4; 7.5 mM $MgCl_2$, 1 mM EDTA and 0.4 mM NADP). The measurement was carried out in a photometer at 340 nm. After the base absorption had been recorded, the enzyme reaction was started by addition of 2 units glucose-6-phosphate dehydrogenase (from *Leuconostoc mesenteroides*, Boehringer Mannheim). The change in absorption is due to an equimolar conversion of glucose-6-phosphate and NADP into 6-phosphogluconate and NADPH, the formation of the NADPH being recorded at the abovementioned wavelength. The reaction was monitored until a plateau had been reached. The result of this measurement gives the glucose-6-phosphate content in the hydrolysate. The degree of hydrolysis was determined from the identical hydrolysate with reference to the content in liberated glucose. The degree of hydrolysis is used for relating the glucose-6-phosphate content to the percentage of hydrolyzed starch from the amount of fresh weight. To this end, 10 µl of hydrolysate were neutralized with 10 µl of 0.7 M NaOH and subsequently diluted 1:100 with water. 4 µl of this dilution were treated with 196 µl of measuring buffer (100 mM imidazole pH 6.9; 5 mM $MgCl_2$, 1 mM ATP, 0.4 mM NADP) and used for determining the base absorption. The reaction was monitored by addition of 2 µl of enzyme mix (hexokinase 1:10; glucose-6-phosphate dehydrogenase from yeast 1:10 in measuring buffer) and at 340 nm until the plateau had been reached. The principle of the measurement corresponds to that of the first reaction.

The result of this measurement gives the amount of glucose (in mg) which had been liberated during the hydrolysis from the starch present in the starting material.

Thereafter, the results of the two measurements are related to one another in order to express the glucose-6-phosphate content per mg of hydrolyzed starch. As opposed to when relating the amount of glucose-6-phosphate to the fresh weight of the sample, this calculation relates the amount of glucose-6-phosphate only to that part of the starch which had been hydrolyzed fully to give glucose and which can thus also be configured as the source of the glucose-6-phosphate.

15) Determination of the Resistant Starch Content (Digestibility)

The resistant starch content is determined by a method based on that described by Englyst et al. (1992, Europ. J. of Clinical Nutrition, 46/2: 33-50) with modifications as described below.

The enzyme solution is prepared by extracting 1.2 g of pancreatin (Merck) in 8 ml of water at 37° C. for 10 minutes. After centrifugation (3000 rpm; RT, 10"), 5.4 ml of the supernatant are mixed with 84 U of amyloglucosidase (Sigma-Aldrich, Taufkirchen) and made up to a final volume of 7 ml with water.

In parallel, 10 mg of rice starch per sample (fresh weight) are mixed in a 2 ml reaction vessel with 0.75 ml of sodium acetate buffer (0.1 M sodium acetate, pH 5.2; 4 mM $CaCl_2$) and incubated at 37° C. for 5 minutes to warm the mixture.

Digestion of the starch is started by adding 0.25 ml of enzyme solution to each mixture. A control mixture has water instead of enzyme solution added. 100 µl aliquots are removed after 20, 60 and 120 minutes and directly added to four times the volume of ethanol, thus inactivating the enzymes. This dilution is used to measure the glucose content.

For this purpose, 2 µl of diluted sample are mixed with 200 µl of measuring buffer (100 mM imidazole/HCl pH 6.9, 5 mM $MgCl_2$, 1 mM ATP, 2 mM NADP), and the absorption of the sample at 340 nm is measured. The conversion of glucose is started by adding 2 µl of enzyme mix (10 µl of hexokinase, 10 µl of glucose-6-phosphate dehydrogenase, 80 µl of measuring buffer) and the equimolar conversion of NADP to NADPH is followed at 340 nm until a plateau is reached. The relation between the measured amounts of glucose and the starch dry weight (calculated from the fresh weight minus water content) yield the proportion of the sample which was liberated as glucose after the appropriate period.

The amount of resistant starch was calculated as follows:

$$RS[\%] = 100 \times \text{deliberated glucose(mg)/Starch dry weight(mg)}$$

EXAMPLES

Example 1

Transformation Vector for Expressing a Wheat Starch Synthase IIa in Rice

The rice transformation vector IR103-123 (described in WO 05/030941) and the plasmid CF31-191 (described in WO 97/45545 under the name pTaSS1) were used. The rice transformation vector IR103-123 serves for the endosperm-specific expression of the target gene by means of the globulin promoter from rice. In a first step a), the vector IR103-123 is linearized using the restriction enzymes EcoRV and XhoI. The plasmid CF31-191 contains the cDNA of a starch synthase II (SSII) from wheat (*Triticum aestivum*). In a second step b), the cDNA of the SSII is excised from the plasmid CF31-191 using the restriction enzymes EcI136II and XhoI. Ligation of the vector IR103-123 which had been linearized in step a) and the fragment, obtained in step b), of plasmid CF 31-191 gives the vector AH32-191.

Example 2

Generation of Genetically Modified Rice Plants with an Increased SSII Activity

To generate genetically modified plants with an increased starch synthase II (SSII) activity, the T-DNA of the plasmid AH32-191 was transferred into rice plants with the aid of *agrobacteria* as described by Ishida et al. (1996, Nature Biotechnology 14 (6): 745-750). The increase of the SSII activity is determined by means of zymograms.

Figure 1B:
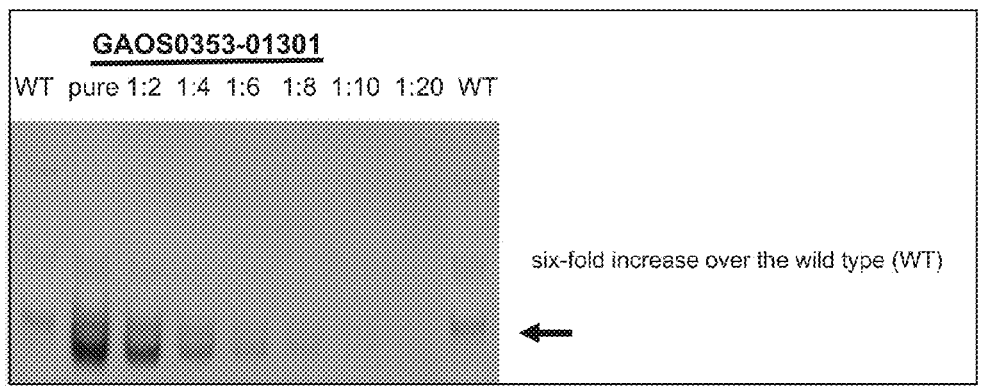
Figure 1C:
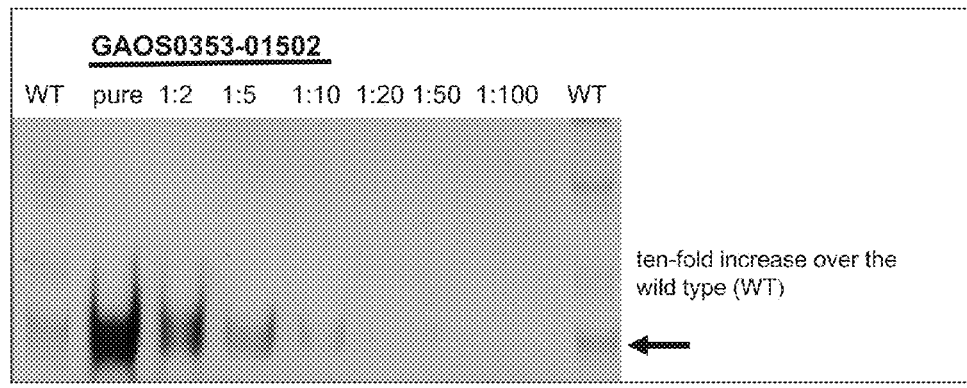

FIG. 1 shows zymograms of three genetically modified rice lines for determining the SSII activity in comparison with the wild type. The material used was total protein extract from immature grains (15 days after the beginning of flowering) of the wild type and the respective genetically modified lines, in each case in identical amounts. The protein extracts from the genetically modified lines were diluted stepwise, and the extent to which the activity was increased was determined by visually comparing the intensity of the SSII band in these lanes with the "wild-type lane". The SSII activity of line GAOS0353-01502 is ten times as high as in the grains of the wild type, that of line GAOS0353-01301 six times as high and that of line GAOS0353-02301 twice as high.

Example 3

Characteristics of Rice Starch from Different Transgenic Lines with a Different SSII Activity Level Rice grains were harvested from plants generated as described in example 2 and subsequently processed by means of the above-described method ("4) Processing of rice grains") to give rice flour. The starch component of the rice flour was subsequently analyzed by means of the above-described method ("7) Determination of the phosphate content in the C6 position (C6-P content)") for their phosphate content in the C6 position.

TABLE 1

Characteristics of rice starch with increased SSII activity

| Line | SS2 expression (xtimes of wt) | C-6-P (in % of wt) |
|---|---|---|
| Wild type | 1 | 100 |
| GAOS0353-01301 | 6 | 184 |
| GAOS0353-02501 | 10 | 358 |

Table 1: Characteristics of rice starch with increased SSII activity in comparison with the wild type (wt). The data shown are the SSII activity (as a multiple of the wild type) and the content of starch-bound glucose-6-phosphate (C-6-P).

It can be seen that the activity level of the starch synthase II correlates with the level of the phosphate content in the C6 position. The expression of line GAOS0353-01301 is increased by a factor of 6, and the C-6-P content has almost doubled in comparison with the wild type. The most pronounced effect is shown by line GAOS0353-02501, whose SSII expression is increased by a factor of 10 and whose C6-P content is increased to over 350% in comparison with the wild type (100%).

Example 4

List of the Properties of Rice Grains, Rice Starch and Rice Flour of Different Genetically Modified Lines with Different Levels of SSII Expression

TABLE 2

Properties of rice starch from rice grains with modified SSII expression in comparison with the wild type:

| Line | SSII expression (x times of WT) | Increased AP-SC range | Reduced AP-SC range | C6P (nmol/mg starch) | DSC $T_{onset}$ | DSC $T_{Peak}$ | DSC $T_{onset}$ (%) | DSC $T_{Peak}$ (%) |
|---|---|---|---|---|---|---|---|---|
| Wild type | 1 | x | x | 0.50 | 64.1 | 69.5 | 100 | 100 |
| GAOS0353-02301 | 2 | 10-26 | 6-9 | 0.74 | 76.2 | 80.8 | 119 | 116 |
| GAOS0353-01301 | 6 | 11-29 | 6-9 | 0.92 | n.d. | n.d. | n.d. | n.d. |
| GAOS0353-01502 | 10 | 12-31 | 6-10 | 1.80 | 77.6 | 82.5 | 121 | 119 |

The data given are the SSII activity in the immature rice grain (as multiples of the wild type), the ranges of the amylopectin side chains of the starch (AP-SC) which are modified significantly over the wild type, the phosphate content (C6P) and the DSC values in ° C. and in % of rice starch (in comparison with the wild type). (n.d.=not detected).

The phosphate content at the C6 position of the starches from genetically modified lines are significantly increased in comparison with the wild type as a function of the level of the SSII activity.

TABLE 3

Properties of rice flour from rice grains with modified SSII expression in comparison with the wild type.

| Line | SSII expression (x times of WT) | DSC $T_{onset}$ | DSC $T_{Peak}$ | DSC $T_{onset}$ (%) | DSC $T_{Peak}$ (%) | Amylose (%) | Amylose (% WT) |
|---|---|---|---|---|---|---|---|
| Wild type | 1 | 65.6 | 71.5 | 100 | 100 | 14.0 | 100 |
| GAOS0353-02301 | 2 | 77.4 | 82.0 | 118 | 115 | 12.5 | 89 |

TABLE 3-continued

Properties of rice flour from rice grains with modified SSII expression in comparison with the wild type.

| Line | SSII expression (x times of WT) | DSC $T_{onset}$ | DSC $T_{Peak}$ | DSC $T_{onset}$ (%) | DSC $T_{Peak}$ (%) | Amylose (%) | Amylose (% WT) |
|---|---|---|---|---|---|---|---|
| GAOS 0353-01301 | 6 | 77.6 | 82.5 | 118 | 115 | 12.5 | 89 |
| GAOS 0353-01502 | 10 | 78.8 | 84.6 | 120 | 118 | 11.7 | 84 |

The data given are the SSII expression in the immature rice grain (as multiples of the wild type), the changes in the DSC values of rice flour, in ° C. and in percent (%) of the wild type.

The apparent amylose contents of the genetically modified lines only show minor modifications; all of them are slightly lower than those of the wild type.

The thermal stability, both of the rice flours and of the starches isolated therefrom, increases gradually in the different genetically modified lines as a function of the SSII activity (compare FIG. 1 and tables 1 and 2). The highest manifestation of the increased DSC T-onset and DSC T-peak is shown by the line whose SSII activity is increased ten-fold. The data are in each case approximately 120%, based on the wild type.

Example 5

Comparison of Different Genetically Modified Rice Lines with Regard to Activity Level and Amylopectin Side Chains in Comparison with the Wild Type (WT)

Table 4 shows the distribution of the amylopectin side chains of different genetically modified rice lines in comparison with the wild type. The curves shown are the result of plotting the chain length (in DP=Degree of Polymerization) of the analyzed glucans versus the percentage of particular DP of the total of all DPs tested.

TABLE 4

Distribution of the side-chain profile of amylopectin of the genetically modified lines in comparison to the wild-type (WT) flour, divided into groups with different degree of polymerization.

| Degree of polymerization (dp) | % based on WT flour | | |
|---|---|---|---|
|  | GAOS0353-2301 | GAOS 0253-1301 | GAOS 0253-1502 |
| dp 6-10 | 81.4 | 66.3 | 47.0 |
| dp 20-25 | 108.7 | 115.7 | 123.8 |

It can be seen that an increasing SSII activity entails a discrete change in the amylopectin side-chain distribution. An increase in the SSII activity results in a gradually, differently pronounced reduction of the side chains with a DP of between 6-10 and an increase in the side chains with a DP of 20-25.

Example 6

Texture of Cooked Rice Grains

Rice grains of different genetically modified lines and of the corresponding wild type were cooked for up to the optimal cooking time in question (see method "determination of the characteristics of cooked rice grains"). The texture is determined on rice grains which, after cooking, had been stored for 22 hours at 4° C. (table 5a, data shown are the means of 10 measurements per sample (in each case 3 grains)) or on freshly cooked rice grains (approximately 1 hour after cooking) and on rice grains which had been stored in the cold (4° C., 22 h) and then reheated in an oven or microwave (table 5b).

TABLE 5a

Texture of rice grains which had been stored for 22 hours at 4° C. after cooking

| Sample | Force 2 (stickiness in g) | Force 1 (grain hardness in g) |
|---|---|---|
| Mean wild-type M202 | −239.5 | 1164.6 |
| Mean GAOS0353-02301 | −137.0 | 1393.0 |
| Mean GAOS0353-01301 | −82.0 | 1775.4 |
| Mean GAOS0353-01502 | −18.3 | 1735.3 |

The stickiness of the cooked rice grains decreases with increasing SSII activity (table 5a). The reduction of the stickiness in line GAOS0353-02301 is reduced to approximately half, in line GAOS0353-01301 by approximately a factor of 3 and in line GAOS0353-01502 approximately by a factor of 13.

TABLE 5b

Texture of freshly cooked or reheated rice grains

| Processing of the test grains | Sample | Stickiness (g) | Stickiness (%) |
|---|---|---|---|
| Freshly cooked | Wild type M202 | −235.8 | 100.0 |
|  | GAOS0353-01502 | −121.4 | 51.5 |
| Reheated in the oven, 80° C./5 min | Wild type M202 | −230.5 | 100.0 |
|  | GAOS0353-01502 | −95.0 | 41.2 |
| Reheated in a microwave, 600 W/3 min | Wild type M202 | −182.2 | 100.0 |
|  | GAOS0353-01502 | −85.3 | 46.8 |

Compilation of the data for determining the stickiness of cooked rice grains after cooking and reheating in the oven or microwave (after storage for 22 hours at 4° C.). In each processing variant, the stickiness of line GAOS0353-01502 is markedly lower than that of the wild type.

Example 7

Determination of the Grain Dimensions of Uncooked and Cooked Rice Grains

The grain dimensions of uncooked and cooked rice grains of genetically modified lines and of the corresponding wild type were determined using the SigmScan software. The results and the parameters derived therefrom are shown in tables 5a and b.

TABLE 6a

Compilation of the data for determining the grain dimensions of uncooked and cooked rice grains.

|  | Wild type | GAOS0353-02301 | GAOS0353-01301 | GAOS0353-01502 |
|---|---|---|---|---|
| Lu (in mm) | 5.36 | 4.81 | 4.94 | 4.87 |
| Wu (in mm) | 2.60 | 2.58 | 2.65 | 2.50 |

TABLE 6a-continued

Compilation of the data for determining the grain
dimensions of uncooked and cooked rice grains.

|  | Wild type | GAOS0353-02301 | GAOS0353-01301 | GAOS0353-01502 |
|---|---|---|---|---|
| Lc (in mm) | 7.59 | 7.50 | 8.18 | 7.87 |
| Wc (in mm) | 3.74 | 3.61 | 3.23 | 3.26 |
| ER | 1.41 | 1.56 | 1.65 | 1.62 |
| Lc/Wc | 2.05 | 2.10 | 2.56 | 2.43 |
| CDC | 2.20 | 2.95 | 4.92 | 4.39 |

The data shown are the means of 30 independent measurements (L = grain length; W = grain width; u = uncooked; c = cooked; ER = elongation rate (Lc/Lu): CDC = coefficient of dimensional changes (Lc/Lu)/(Wc/Wu)).

TABLE 6b

Relative changes of the grain dimensions
in comparison with the wild type

|  | Wild type | GAOS0353-02301 | GAOS0353-01301 | GAOS0353-01502 |
|---|---|---|---|---|
| Lu | 0 | −10.3 | −7.8 | −9.1 |
| Wu | 0 | −0.8 | 1.9 | −3.8 |
| Lc | 0 | −1.2 | 7.8 | 3.7 |
| Wc | 0 | −3.5 | −13.6 | −12.8 |
| ER | 0 | 10.6 | 17.0 | 14.9 |
| Lc/Wc | 0 | 2.4 | 24.9 | 18.5 |
| CDC | 0 | 34.1 | 123.6 | 99.5 |

All data in percent: % change = (sample − wild type)/wild type * 100).

As regards the grain dimensions of cooked rice grains, the increased SSII activity in rice results in a significantly higher elongation of the grains during cooking along the longitudinal axis. This is clear from the increased elongation rate (ER) and the increased length/width ratio (Lc/Wc). Again, the line whose SSII activity is increased twofold (GAOS0353-02301) shows a lesser degree of change with regard to the above-described parameters, while the two lines whose SSII activities are six-fold (GAOS0353-01301) or ten-fold (GAOS0353-01502) increased show much more pronounced manifestations.

Example 8

Analysis of the Physico-Chemical Characteristics of Rice Flour by Means of Rapid Visco Analyzer (RVA)

Rice flours from different genetically modified lines and from the corresponding wild type were analyzed for their physico-chemical characteristics as described in the method "analysis of rice flour by means of RVA".

The viscosity of the rice-flour/water suspension was recorded over a defined temperature and shearing program. The graphs and analytical data of the different lines are shown in tables 6a+b.

TABLE 7a

Compilation of the data obtained in the determination of the
viscosity behavior of rice flours made with rice grains from
genetically modified lines with differing SSII activities

| Sample: | Wild type | 353-02301 | 353-01301 | 353-01502 |
|---|---|---|---|---|
| Peak viscosity (cP) | 4767 | 4626 | 4322 | 3787 |
| Trough (cP) | 2122 | 1755 | 1647 | 1515 |
| Breakdown (cP) | 2645 | 2871 | 2675 | 2272 |
| End viscosity (cP) | 2934 | 2338 | 2249 | 2065 |
| Setback (cP) | 812 | 583 | 602 | 550 |
| Setback rice (cP) | −1833 | −2288 | −2073 | −1722 |
| Peak Time (min) | 5.36 | 5.02 | 5.04 | 4.56 |
| Pasting temperature (° C.) | 72.8 | 82.3 | 81.7 | 83.9 |
| Pasting Time (min) | 2.56 | 3.36 | 3.4 | 3.48 |
| Peak Time − Pasting Time (sec) | 144.0 | 73.2 | 76.8 | 64.8 |

TABLE 7b

Relative changes of the RVA parameters
in comparison with the wild type

| Sample: | Wild type | 353-02301 | 353-01301 | 353-01502 |
|---|---|---|---|---|
| Peak viscosity (cP) | 0.0 | −3.0 | −9.3 | −20.6 |
| Trough (cP) | 0.0 | −17.3 | −22.4 | −28.6 |
| Breakdown (cP) | 0.0 | 8.5 | 1.1 | −14.1 |
| End viscosity (cP) | 0.0 | −20.3 | −23.3 | −29.6 |
| Setback (cP) | 0.0 | −28.2 | −25.9 | −32.3 |
| Setback rice (cP) | 0.0 | 24.8 | 13.1 | −6.1 |
| Peak Time (min) | 0.0 | −9.5 | −9.5 | −12.0 |
| Pasting temperature (° C.) | 0.0 | 13.0 | 12.2 | 15.2 |
| Pasting Time (min) | 0.0 | 32.8 | 31.3 | 35.9 |
| Peak Time − Pasting Time (min) | 0.0 | −49.2 | −46.7 | −55.0 |

(all data in percent) % change = (sample − wild type)/wild type * 100

The course of the viscosity of flours from the wild type and the genetically modified lines differs in a plurality of parameters. The genetically modified samples start pasting at a markedly later point in time, which can be seen from the increased "pasting temperature". The subsequent development of the viscosity up to the peak viscosity proceeds very rapidly, as can be seen from the shorter "peak time" of the genetically modified samples. All the other viscosity parameters (peak, trough, final) are lower in the case of the genetically modified samples than in the case of the wild type. It must be mentioned here that the extent of the changes over the wild type correlates with the level of the SSII activity. The line with the highest SSII activity (GAOS0353-1502) shows the lowest peak, trough and final viscosities and, with a value of more than 10° C., the highest difference in the pasting temperature.

Another, very obvious aspect is the rapid development of the viscosity of the genetically modified samples, which is reflected in a very brief interval between the onset of pasting and the time of peak viscosity. Again, this parameter shows a pronounced dependence of the effect on the degree by which the SSII activity is increased.

Example 9

Digestibility of Isolated Starch

The starches of the transformants GAOS353-2501 and GAOS 353-1301 show a distinctly reduced digestibility compared with the wild type.

The enzymatic degradation of the isolated starch in the case of the transformant GAOS 353-1301 relative to the wild type is 53% after 20 minutes, 67% after 60 minutes and 84% after 120 minutes.

Figure 3:
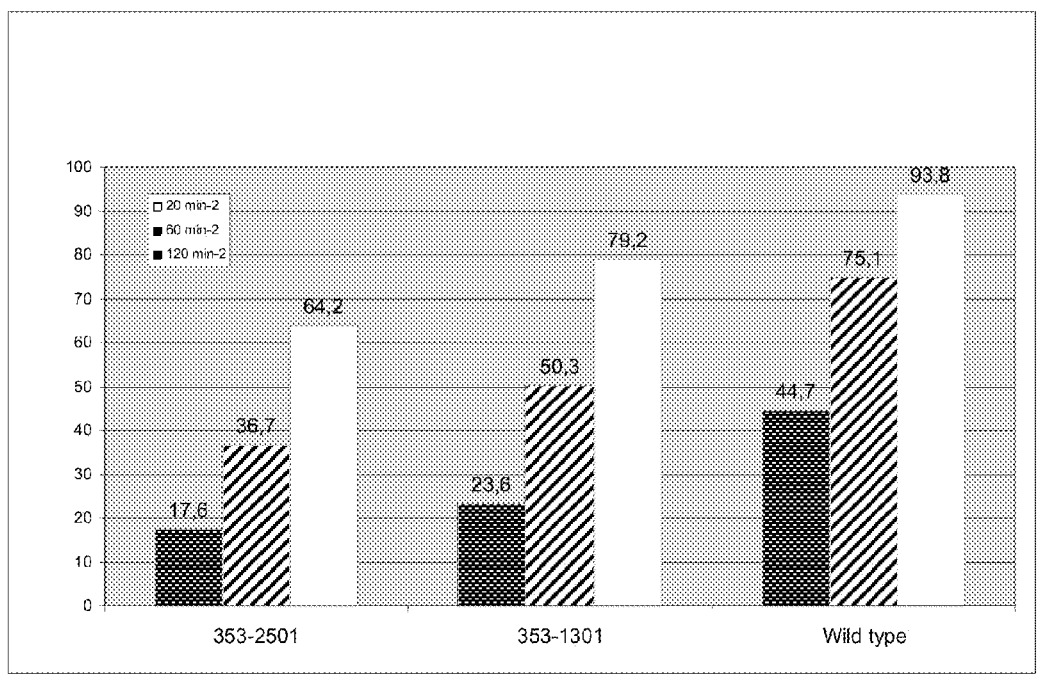
FIG. 3 shows digestibility of isolated starch from rice flour after 20, 60 and 120 minutes (measured as liberated glucose as percentage of the starch dry weight) of wild type rice and transformants GAOS353-1301 and GAOS353-2501.

The enzymatic degradation of the isolated starch in the case of the transformant GAOS 353-2501 relative to the wild type is 39% after 20 minutes, 49% after 60 minutes and 68% after 120 minutes (FIG. 3).

TABLE 8

RS content of rice starches

| | RS content (%) |
|---|---|
| Wildtype | 6.2 |
| 353-2501 | 35.8 |
| 353-1301 | 20.8 |

The invention claimed is:

1. A process for increasing the phosphate content of starches of genetically modified rice plant cells to 150 to 380% in comparison with starches from corresponding wild-type rice plant cells (100%), comprising overexpressing a foreign nucleic acid molecule coding for a soluble starch synthase II in a genetically modified rice plant cell, wherein expression of soluble starch synthase II in said genetically modified rice plant cell is increased six to ten times compared to expression of soluble starch synthase II in a corresponding wild-type rice plant cell.

2. The process of claim 1, wherein the foreign nucleic acid molecule comprises the coding region of a heterologous soluble starch synthase II.

3. The process of claim 1, wherein the soluble starch synthase II is a soluble starch synthase II from a monocotyledonous plant.

4. The process of claim 1, wherein the soluble starch synthase II is a soluble starch synthase II from wheat.

5. The process of claim 1, wherein the soluble starch synthase II comprises the nucleotide sequence of SEQ ID No. 1.

6. The process of claim 1, wherein said process increases the phosphate content of said starches of genetically modified rice plant cells to 160 to 380% in comparison with starches from corresponding wild-type plant cells (100%).

7. A rice starch comprising a DSC T-onset temperature of between 70° C. and 80° C. and a phosphate content at position C6 between 0.9 and 2.5 nmol phosphate per milligram of starch, wherein said rice starch is obtained from a genetically modified rice plant cell that overexpresses a foreign nucleic acid molecule coding for a soluble starch synthase II, and wherein said expression of soluble starch synthase II in said genetically modified rice plant cell is increased six to ten times compared to expression of soluble starch synthase II in a corresponding wild-type rice plant cell.

8. The rice starch of claim 7, wherein the DSC T-onset temperature is between 72° C. and 79° C.

9. A derivatized rice starch comprising the rice starch of claim 7.

10. A composition comprising the rice starch of claim 7.

11. A rice flour comprising the rice starch of claim 7.

12. A composition comprising the rice flour of claim 10.

13. A rice grain comprising the rice starch of claim 7.

14. A composition comprising at least one rice grain of claim 13.

15. A rice plant comprising at least one rice grain of claim 13.

16. A foodstuff comprising the rice flour of claim 11.

17. An animal feed comprising the rice flour of claim 11.

18. The rice starch of claim 7, further comprising a resistant starch (RS) content of 15-45%.

19. The starch of claim 18, wherein said resistant starch (RS) content is 17-40%.

20. The starch of claim 19, wherein said resistant starch (RS) content is 20-38%.

21. The process of claim 1, wherein said process increases the phosphate content of said starches of genetically modified rice plant cells to 170 to 380% in comparison with starches from corresponding wild-type plant cells (100%).

22. The process of claim 1, wherein expression of soluble starch synthase II in said genetically modified rice plant cell is increased six times compared to expression of soluble starch synthase II in a corresponding wild-type rice plant cell.

23. A genetically modified rice grain comprising an overexpressed foreign nucleic acid molecule coding for a soluble starch synthase II, wherein starch from said rice grain comprises:
    (a) a phosphate content at position C6 between 0.9 and 2.5 nmol phosphate per milligram of starch; and/or
    (b) a content of amylopectin side chains with a DP of 6-10 decreased by 20-60% in comparison with rice starch from corresponding wild-type rice plants,
    wherein expression of soluble starch synthase II in said genetically modified rice grain is increased six to ten times compared to expression of soluble starch synthase II in a corresponding wild-type rice grain.

24. The rice grain of claim 23, wherein said starch comprises a content of amylopectin side chains with a DP of 6-10 decreased by 25-55% in comparison with rice starch from corresponding wild-type rice plants.

25. The rice grain of claim 23, wherein said starch comprises a phosphate content at position C6 between 1.5 and 2.5 nmol phosphate per milligram of starch.

26. The rice grain of claim 23, wherein said starch comprises a content of amylopectin side chains with a DP of 6-10 decreased by 30-60% in comparison with rice starch from corresponding wild-type rice plants.

27. Rice grains obtained from a genetically modified rice plant comprising an overexpressed foreign nucleic acid molecule coding for a soluble starch synthase II, wherein expression of soluble starch synthase II in said genetically modified rice plant is increased six to ten times compared to expression of soluble starch synthase II in a corresponding wild-type rice plant, and
    wherein said rice grains, when cooked, comprise:
    (a) a stickiness of −10 to −130 g measured in grams of tensile force;
    (b) an elongation rate increased by 14% to 18% compared to cooked rice grains from corresponding wild-type rice plants; and/or
    (c) a coefficient of dimensional changes (CDC) value of 3.5 to 5.5.

28. The rice grains of claim 27, wherein said rice grains, when cooked, have a stickiness of −15 to −130 g measured in grams of tensile force.

29. The rice grains of claim 27, wherein said rice grains, when cooked, have a CDC value of 4 to 5.

30. The process of claim 1, wherein expression of soluble starch synthase II in said genetically modified rice plant cell is increased ten times compared to expression of soluble starch synthase II in a corresponding wild-type rice plant cell.

31. The rice starch of claim 7, wherein said starch comprises a phosphate content at position C6 between 1.5 and 2.5 nmol phosphate per milligram of starch.

32. The rice starch of claim 7, wherein said starch comprises a phosphate content at position C6 between 1.5 and 2.0 nmol phosphate per milligram of starch.

33. The rice grain of claim 23, wherein said starch comprises a phosphate content at position C6 between 1.5 and 2.0 nmol phosphate per milligram of starch.

34. A process for increasing the phosphate content of starches of genetically modified rice plant cells to 150 to 380% in comparison with starches from corresponding wild-type rice plant cells (100%), comprising overexpressing a foreign nucleic acid molecule coding for a wheat soluble starch synthase II in a genetically modified rice plant cell.

35. A rice starch comprising a DSC T-onset temperature of between 70° C. and 80° C. and a phosphate content at position C6 between 0.9 and 2.5 nmol phosphate per milligram of starch, wherein said rice starch is obtained from a genetically modified rice plant cell that overexpresses a foreign nucleic acid molecule coding for a wheat soluble starch synthase II.

36. A genetically modified rice grain comprising an overexpressed foreign nucleic acid molecule coding for a wheat soluble starch synthase II, wherein starch from said rice grain comprises:
   (a) a phosphate content at position C6 between 0.9 and 2.5 nmol phosphate per milligram of starch; and/or
   (b) a content of amylopectin side chains with a DP of 6-10 decreased by 20-60% in comparison with rice starch from corresponding wild-type rice plants.

37. Rice grains obtained from a genetically modified rice plant comprising an overexpressed foreign nucleic acid molecule coding for a soluble starch synthase II,
   wherein said rice grains, when cooked, comprise:
   (a) a stickiness of −10 to −130 g measured in grams of tensile force;
   (b) an elongation rate increased by 14% to 18% compared to cooked rice grains from corresponding wild-type rice plants; and/or
   (c) a coefficient of dimensional changes (CDC) value of 3.5 to 5.5.

* * * * *